US012246048B2

(12) United States Patent
Kwon et al.

(10) Patent No.: US 12,246,048 B2
(45) **Date of Patent: *Mar. 11, 2025**

(54) RECOMBINANT HERPES SIMPLEX VIRUS HAVING MODIFIED GLYCOPROTEIN GH FOR RETARGETING AND USE THEREOF

(71) Applicant: Gencellmed Inc., Seoul (KR)

(72) Inventors: Heechung Kwon, Gyeonggi-do (KR); Hyunjung Baek, Gyeonggi-do (KR)

(73) Assignee: Gencellmed Inc., Seoul (KR)

( * ) Notice: Subject to any disclaimer, the term of this patent is extended or adjusted under 35 U.S.C. 154(b) by 762 days.

This patent is subject to a terminal disclaimer.

(21) Appl. No.: 17/430,018

(22) PCT Filed: Feb. 19, 2021

(86) PCT No.: PCT/KR2021/002154

§ 371 (c)(1),
(2) Date: Aug. 11, 2021

(87) PCT Pub. No.: WO2021/251588

PCT Pub. Date: Dec. 16, 2021

(65) Prior Publication Data

US 2022/0305067 A1 Sep. 29, 2022

(30) Foreign Application Priority Data

Jun. 12, 2020 (KR) ........................ 10-2020-0071873
Jun. 16, 2020 (KR) ........................ 10-2020-0072979

(51) Int. Cl.

| | |
|---|---|
| ***A61K 35/763*** | (2015.01) |
| ***A61P 29/00*** | (2006.01) |
| ***A61P 35/00*** | (2006.01) |
| ***C07K 14/705*** | (2006.01) |
| ***C07K 16/32*** | (2006.01) |
| ***C12N 7/00*** | (2006.01) |

(52) U.S. Cl.
CPC ............ *A61K 35/763* (2013.01); *A61P 29/00* (2018.01); *A61P 35/00* (2018.01); *C07K 14/705* (2013.01); *C07K 16/32* (2013.01); *C12N 7/00* (2013.01)

(58) Field of Classification Search
CPC ........ A61K 35/763; A61P 29/00; A61P 35/00; C07K 14/705; C07K 16/32; C12N 7/00
See application file for complete search history.

(56) References Cited

U.S. PATENT DOCUMENTS 5,821,337 A * 10/1998 Carter .................... C07K 16/28 530/387.3
7,033,798 B2 * 4/2006 Pluckthun .......... A61K 47/6825 435/69.6
9,593,347 B2 * 3/2017 Glorioso, III ............ C12N 7/00
11,421,017 B2 * 8/2022 Kwon .................. C07K 16/087
2010/0233758 A1 * 9/2010 Kwon .............. C07K 14/70578 435/235.1
2013/0224154 A1 * 8/2013 Marchini ................. C12N 7/00 435/235.1
2016/0153000 A1 * 6/2016 Glorioso ................... A61P 7/00 435/456
2018/0002723 A1 * 1/2018 Campadelli ............ C12N 15/86
2019/0300862 A1 10/2019 Nicosia et al.
2022/0305066 A1 * 9/2022 Kwon .................. C07K 14/705

FOREIGN PATENT DOCUMENTS

CN 104126009 A 10/2014
CN 106068326 A 11/2016
EP 3256570 B1 3/2021
WO WO-2017/040801 A2 3/2017

OTHER PUBLICATIONS

Menotti, L., Avitabile, E., Gatta, V., Malatesta, P., Petrovic, B., & Campadelli-Fiume, G. (2018). HSV as A Platform for the Generation of Retargeted, Armed, and Reporter-Expressing Oncolytic Viruses. Viruses, 10(7), 352. (Year: 2018).*

Kolb, A. W., Adams, M., Cabot, E. L., Craven, M., & Brandt, C. R. (2011). Multiplex sequencing of seven ocular herpes simplex virus type-1 genomes: phylogeny, sequence variability, and SNP distribution. Investigative Ophthalmology & Visual Science, 52(12), 9061-9073. (Year: 2011).*

Kolb et al. (2011). Direct Submission. Submitted Aug. 1, 2011. GenBank: AER37815.1. (Year: 2011).*

Wang, K. et al. (2012). A herpes simplex virus 2 glycoprotein D mutant generated by bacterial artificial chromosome mutagenesis is severely impaired for infecting neuronal cells and infects only Vero cells expressing exogenous HVEM. Journal of virology, 86(23), 12891-12902. (Year: 2012).*

Baek, H., Uchida, H., Jun, K., Kim, J. H., Kuroki, M., Cohen, J. B., Glorioso, J. C., & Kwon, H. (2011). Bispecific adapter-mediated retargeting of a receptor-restricted HSV-1 vector to CEA-bearing tumor cells. Molecular therapy : the journal of the American Society of Gene Therapy, 19(3), 507-514. (Year: 2011).*

Campadelli-Fiume, G., Petrovic, B., Leoni, V., Gianni, T., Avitabile, E., Casiraghi, C., & Gatta, V. (2016). Retargeting Strategies for Oncolytic Herpes Simplex Viruses. Viruses, 8(3), 63-63. (Year: 2016).*

(Continued)

*Primary Examiner* — Janet L Andres
*Assistant Examiner* — Carey Alexander Stuart
(74) *Attorney, Agent, or Firm* — Harness, Dickey & Pierce, P.L.C.

(57) ABSTRACT

Proposed are a recombinant herpes simplex virus having a modified glycoprotein gH for retargeting and the use thereof. Particularly, the recombinant herpes simplex virus is capable of infecting a target cell having a target molecule to which a cell-targeting domain specifically recognizes and binds due to the presence of the cell-targeting domain in the glycoprotein gH thereof, and is thus useful for anticancer therapy or gene therapy.

18 Claims, 8 Drawing Sheets

Specification includes a Sequence Listing.

(56) References Cited

OTHER PUBLICATIONS

Leoni, V., Gatta, V., Casiraghi, C., Nicosia, A., Petrovic, B., & Campadelli-Fiume, G. (2017). A Strategy for Cultivation of Retargeted Oncolytic Herpes Simplex Viruses in Non-cancer Cells. Journal of Virology, 91(10). (Year: 2017).*

Office Action from corresponding Japanese Patent Application No. 2023-509358, dated Nov. 6, 2023.

Menotti, L., et al.; "HSV as A Platform for the Generation of Retargeted, Armed, and Reporter-Expressing Oncolytic Viruses", Viruses, 2018, 10, 352, pp. 1-30.

Wang, K., et al.; "A Herpes Simplex Virus 2 Glycoprotein D Mutant Generated by Bacterial Artificial Chromosome Mutagenesis Is Severly Impaired for Infecting Neuronal Cells and Infects Only Vero Cells Expressing Exogenous HVEM", Journal of Virology, Dec. 2012, vol. 86, No. 23, p. 12893-12902.

Examination Report from corresponding Australian Patent Application No. 2021287122, dated Aug. 22, 2024.

Gatta, V., et al.; "The Engineering of a Novel Ligand in gH Confers to HSV an Expanded Tropism Independent of gD Activation by Its Receptors", PLoS Pathog 11(5):e1004907, pp. 1-18, 2015.

Examination Report from corresponding Australian Patent Application No. 2021287122, dated Apr. 24, 2024.

Baek, H., et al., "Bispecific Adapter-Mediated Retargeting of a Receptor-Restricted HSV-1 Vector to CEA-Bearing Tumor Cells", Molecular Therapy vol. 19 No. 3, 507-514, Mar. 2011.

Office Action from corresponding Chinese Patent Application No. 202180038257.4, dated Jan. 2, 2025.

* cited by examiner

RECOMBINANT HERPES SIMPLEX VIRUS HAVING MODIFIED GLYCOPROTEIN GH FOR RETARGETING AND USE THEREOF

CROSS-REFERENCE TO RELATED APPLICATIONS

This application is a national phase application of PCT Application No. PCT/KR2021/002154, filed on Feb. 19, 2021, which claims priority to Korean Patent Application Nos. 10-2020-0072979 filed on Jun. 16, 2020, and 10-2020-0071873, filed on Jun. 12, 2020. The entire disclosure of the applications identified in this paragraph is incorporated herein by reference.

SEQUENCE LISTING

This application contains references to amino acid sequences and/or nucleic acid sequences which have been submitted concurrently herewith as the sequence listing text file entitled "000023usnp_SequenceListing.txt", file size 42,257 bytes, created on 5 Aug. 2024. The aforementioned sequence listing is hereby incorporated by reference in its entirety pursuant to 37 C.F.R. § 1.52 (e) (5).

TECHNICAL FIELD

The present disclosure relates to a recombinant herpes simplex virus having a modified glycoprotein gH for retargeting, and to the use thereof.

BACKGROUND ART

In the treatment of cancer, surgical therapy, anticancer chemotherapy, radiotherapy, and the like have been widely used to date, but most of these are characterized by side effects, incomplete treatment effects, and problems such as cancer recurrence and metastasis. Therefore, the development of new and effective cancer therapies is continually required, and in recent years, rapid advancements have been made in the field of anticancer immunotherapy, examples of which include oncolytic virus therapy, chimeric antigen receptor T (CAR-T) cell therapy, and the like.

In anticancer immunotherapy, an oncolytic virus is a virus imparted with the ability to lyse cancer cells through manipulation of the genes of a living virus and selective propagation thereof in cancer cells, and propagation thereof in normal cells is limited. The virus released by lysis of cancer cells is able to continuously infect surrounding cancer cells, thereby providing a continuous and synergistic therapeutic effect. Moreover, the oncolytic virus is capable of increasing the anticancer effect by stimulating the immune response of the human body by releasing an immunogenic tumor antigen in the process of lysing cancer cells. Furthermore, such anticancer effects may be enhanced through artificial manipulation so as to express cytokines, chemokines, and the like.

Currently developed oncolytic viruses may be classified into 10 or more types, including adenovirus, herpes simplex virus (HSV), vaccinia virus, etc. Among these, HSV is an enveloped icosahedral virion containing linear double-stranded DNA having a size of 152 kb, and includes HSV-1 and HSV-2 types. HSV has many non-essential genes, and the genome size thereof is large, making it easy to use to manipulate or transport external genes, and the replication cycle thereof is short, and moreover, HSV has high infection efficiency, and is desirably capable of exhibiting improved cancer-cell-targeting efficiency through easy manipulation of glycoproteins involved in cell attachment and infection.

HSV is a virus having an envelope, and the entry of HSV into cells is achieved through complex interactions involving gD, gB, gH/gL and gC glycoproteins present in the envelope thereof. First, when gB and gC are attached to 3-O-S HS (3-O-sulfated heparan sulfate) on the cell surface, gD binds to at least one receptor among cell receptors such as HVEM (herpesvirus entry mediator, HveA), nectin-1 (HveC), and nectin-2 (HveB) to thus induce fusion between the virus and the cell membrane, whereby HSV enters the cells (Hiroaki Uchida et al., Generation of Herpesvirus Entry Mediator (HVEM)-restricted Herpes Simplex Virus Type 1 Mutant Viruses: Resistance of HVEM-expressing Cells and Identification of Mutations That Rescue nectin-1 Recognition. J. Virol. 2009 April; 83 (7): 2951-61).

T-VEC (talimogene laherparepvec, product name: Imlygic), approved by the US FDA in October 2015, is an oncolytic viral therapeutic agent for malignant melanoma using HSV-1. T-VEC is an attenuated HSV-1 virus from which ICP34.5 and ICP47 genes are deleted to attenuate the pathogenicity thereof and which expresses GM-CSF (granulocyte-macrophage-colony-stimulating factor) to promote the human immune response. However, T-VEC has a drawback in that the therapeutic efficacy thereof is low due to the limited viral propagation thereof, attributed to the loss of some genes.

In order to overcome such limitations, attempts have been made to perform retargeting to specifically target cancer cells by manipulating the envelope glycoproteins gD, gB, gH, and gC, which are involved in the entry of HSV into cells, without weakening the virus. This retargeting is the introduction of an exogenous sequence encoding a targeting domain for a cancer cell target molecule into the glycoprotein gD, gB, gH, or gC sequence, and uses a recombinant virus having a chimeric glycoprotein in which a targeting domain (also called a ligand) of an exogenous sequence is inserted into the glycoprotein, rather than a wild-type glycoprotein. Such a recombinant virus is capable of entering cancer cells having a target molecule that is specifically recognized and bound by the targeting domain. The targeting domain is typically an scFv (single-chain variable fragment), and the target molecules that are currently retargeted are EpCAM (epithelial cell adhesion molecule), HER2 (human epidermal growth factor receptor 2), etc., and gB, gH, gC and the like, as glycoproteins, have been modified.

The present disclosure provides a recombinant HSV having a modified glycoprotein gH for retargeting.

SUMMARY

Technical Problem

Therefore, the present disclosure has been made keeping in mind the problems encountered in the related art, and an objective of the present disclosure is to provide a recombinant HSV having a modified glycoprotein gH for retargeting.

Another objective of the present disclosure is to provide a pharmaceutical composition for treating cancer containing the recombinant HSV as an active ingredient.

Still another objective of the present disclosure is to provide a method of preventing or treating cancer including administering the pharmaceutical composition to a subject such as a patient in an effective amount.

Other or specific objectives of the present disclosure will be set forth below.

Technical Solution

The inventors of the present disclosure have ascertained that, as confirmed in the examples below, a recombinant HSV, configured such that scFv, which is a cell-targeting domain (an exogenous ligand that specifically binds to a target molecule of a target cell) that specifically recognizes and binds to HER2, EpCAM, or CEA (carcinoembryonic antigen) as a target molecule of a target cell such as a cancer cell, etc., is inserted and fused into a glycoprotein gH, retargets and infects a target cell expressing HER2, EpCAM or CEA, thus culminating in the present disclosure.

Considering the above, an aspect of the present disclosure pertains to a recombinant HSV obtained by inserting and fusing a cell-targeting domain, which specifically recognizes and binds to a target molecule of a target cell, into a glycoprotein gH.

In general, a recombinant HSV is HSV that is genetically manipulated so as to be capable of losing or altering certain functions or expressing a target protein of interest by introducing an artificial mutation (through deletion, substitution or insertion of some nucleic acid sequences) compared to a wild-type HSV. In the present disclosure, the recombinant HSV is HSV having a cell-targeting domain in a glycoprotein gH for targeting target cells.

Recombinant virus production techniques such as genetic manipulation of viruses and production of virions are well known in the art, and reference may be made to Sandri-Goldin R. M. et al. [Alpha Herpesviruses: Molecular and Cellular Biology, Caister Academic Press, 2006], Robin H. Lachmann [Herpes simplex virus-based vectors, Int. J. Exp. Pathol. 2004 August; 85 (4): 177-190], and the like. All documents cited in the present specification, including the above documents, are considered part of the present specification.

In particular, in addition to the introduction of the targeting domain for the target molecule of the target cell into the glycoprotein gH, the recombinant HSV of the present disclosure may be further manipulated to enter cells only through an HVEM receptor, as an entry receptor, rather than nectin-1. In the following examples of the present disclosure, the sequence of the HSV envelope glycoprotein gD is manipulated to allow HSV to enter cells only through the HVEM receptor. Specifically, arginine (R) at position 222 of gD and phenylalanine (F) at position 223 of gD are substituted with asparagine (N) and isoleucine (I), respectively, so the function of gD is altered. The recombinant HSV having the gD function thus altered may enter host cells only through the HVEM (HveA) receptor (Hiroaki Uchida et al., Generation of Herpesvirus Entry Mediator (HVEM)-restricted Herpes Simplex Virus Type 1 Mutant Viruses: Resistance of HVEM-expressing Cells and Identification of Mutations That Rescue nectin-1 Recognition. J. Virol. 2009 April; 83 (7): 2951-61). The HVEM (HveA) receptor is seldom present in normal cells, and is present only in lymphomas, etc., whereas nectin-1 is usually present in normal cells, so the recombinant HSV having the altered gD function, which may enter cells only through the HVEM receptor, rather than the nectin-1 receptor, does not infect normal cells, and is thus advantageous from the aspect of safety in anticancer therapy.

The recombinant HSV of the present disclosure may be manufactured by deleting or not deleting some genes of the glycoprotein gH thereof and inserting the gene for the cell-targeting domain into the gH gene as an open reading frame. In the case in which the gene of the cell-targeting domain is inserted into the gene of the glycoprotein gH, the cell-targeting domain is integrated into the envelope of a virion when the recombinant HSV is produced in the cells in the state of being fused to the glycoprotein gH.

When the cell-targeting domain is inserted and fused into the gH glycoprotein, the position at which the same is inserted and fused may be any position including the N-terminus of gH, the N-terminus of the H1A domain, etc., and a preferred position for HSV-1 may be, in the amino acid sequence of gH (SEQ ID NO: 1, GenBank Accession No. ASM47773), a position within the region of amino acids 12 to 88, a position within the region of amino acids 116 to 137, or a position within the region of amino acids 209 to 839. In addition, a preferred position may be a position within the region of amino acids 12 to 49 or a position within the region of amino acids 116 to 137. In addition, a preferred position may be a position after amino acid 12, a position after amino acid 22, a position after amino acid 23, a position after amino acid 29, a position after amino acid 83, a position after amino acid 116, a position after amino acid 209, a position after amino acid 215, a position after amino acid 225, a position after amino acid 277, a position after amino acid 386, a position after amino acid 437, a position after amino acid 447, a position after amino acid 472, a position after amino acid 636, a position after amino acid 637, a position after amino acid 666, a position after amino acid 731, a position after amino acid 763, a position after amino acid 764, a position after amino acid 775, a position after amino acid 806, a position after amino acid 824, or a position after amino acid 838. Here, the position is based on the amino acid sequence of SEQ ID NO: 1 of gH, but in the case of a mutant strain having some differences in the sequence of gH, it is based on a homologous sequence corresponding thereto.

In addition, the recombinant HSV of the present disclosure may be manipulated to enable additional targeting through modification of other glycoproteins of HSV, in addition to the modification of the glycoprotein gH. Such additional targeting may be particularly advantageous in terms of efficiency of infection of cancer cells in anticancer therapy, and glycoproteins that may be used for such additional targeting may include gB, gC, gD, and the like.

When the cell-targeting domain is additionally inserted and fused into such a glycoprotein for additional targeting, the position thereof may be any position including the N-terminus of the glycoprotein, but in HSV-1, a preferred position may be any position within the region of amino acids 9 to 896 in the amino acid sequence of gB (SEQ ID NO: 2, GenBank Accession No. ASM47779). In addition, a preferred position may be any position within the region of amino acids 31 to 78, any position within the region of amino acids 80 to 363, or any position within the region of amino acids 408 to 896. In addition, a preferred position may be a position after amino acid 43, a position after amino acid 52, a position after amino acid 70, a position after amino acid 76, a position after amino acid 80, a position after amino acid 81, a position after amino acid 95, a position after amino acid 100, a position after amino acid 137, a position after amino acid 185, a position after amino acid 187, a position after amino acid 241, a position after amino acid 261, a position after amino acid 265, a position after amino acid 304, a position after amino acid 334, a position after amino acid 361, a position after amino acid 408, a position after amino acid 419, a position after amino acid 430, a position after amino acid 458, a position after amino acid 470, a position after amino acid 481, a position after amino acid 495, a position after amino acid 497, a position after amino acid 546, a position after amino acid 608, a position after amino acid 630, a position after amino acid 663, a position after amino acid 664, a position after amino acid 665, a position after amino acid 671, a position after amino acid 673, a position after amino acid 690, a position after amino acid 725, a position after amino acid 730, a position after amino acid 732, a position after amino acid 742, a position after amino acid 772, a position after amino acid 868, a position after amino acid 869, a position after amino acid 886, a position after amino acid 893, a position after amino acid 894, or a position after amino acid 895 of gB. Here, the position is based on the amino acid sequence of SEQ ID NO: 2 of gB, but in the case of a mutant strain having some differences in the sequence of gB, it is based on a homologous sequence corresponding thereto.

When the cell-targeting domain is additionally inserted and fused into the gC glycoprotein, the position thereof may be any position including the N-terminus, but in HSV-1, a preferred position may be any position within the region of amino acids 1 to 442 in the amino acid sequence of gC (SEQ ID NO: 3, GenBank Accession No. ASM47796), and moreover, a preferred position may be any position within the region of amino acids 33 to 154. In addition, a preferred position may be a position after amino acid 33, a position after amino acid 82, a position after amino acid 148, a position after amino acid 149, or a position after amino acid 153 of gC. Here, the position is based on the amino acid sequence of SEQ ID NO: 3 of gC, but in the case of a mutant strain having some differences in the sequence of gC, it is based on a homologous sequence corresponding thereto.

For more specific information on the preferred insertion site of the glycoprotein, reference may be made to JOHN R. GALLAGHER et al. [Functional Fluorescent Protein Insertions in Herpes Simplex Virus gB Report on gB Conformation before and after Execution of Membrane Fusion, PLOS Pathog., 2014 Sep. 18, 10 (9): e1004373], Gatta V. et al. [The Engineering of a Novel Ligand in gH Confers to HSV an Expanded Tropism Independent of gD Activation by Its Receptors, PLOS Pathog. 2015 May 21; 11 (5): e1004907], Tina M. Cairns et al. [Structure-Function Analysis of Herpes Simplex Virus Type 1 gD and gH-gL: Clues from gDgH Chimeras, JOURNAL OF VIROLOGY, June 2003, p.6731-6742], E. U. Lorentzen et al. [Replication-Competent Herpes Simplex Virus Type 1 Mutant Expressing an Autofluorescent Glycoprotein H Fused protein, Intervirology 2001; 44:232-242], Qing Fan et al. [Differential Effects on Cell Fusion Activity of Mutations in Herpes Simplex Virus 1 Glycoprotein B (gB) dependent on Whether a gD Receptor or a gB Receptor Is Overexpressed, JOURNAL OF VIROLOGY, August 2009, 83 (15): 7384-7390], Erick Lin et al. [Random linker-insertion mutagenesis to identify functional domains of herpes simplex virus type 1 glycoprotein B, Proc. Natl. Acad. Sci. USA. August 2007, 104 (32): 13140-13145], Julia O. Jackson et al. [Insertion Mutations in Herpes Simplex Virus 1 Glycoprotein H Reduce Cell Surface Expression, Slow the Rate of Cell Fusion, or Abrogate Functions in Cell Fusion and Viral Entry, JOURNAL OF VIROLOGY, February 2010, 84 (4): 2038-2046], Guoying Zhou et al. [Engineered herpes simplex virus 1 is dependent on IL13R*2 receptor for cell entry and independent of glycoprotein D receptor interaction, Proc. Natl. Acad. Sci. USA. November 2002, 99 (23): 15124-15129], AR Frampton Jr. et al. [HSV trafficking and development of gene therapy vectors with applications in the nervous system, Gene Therapy, 2005, 12:891-901], Paola Grandi et al. [HSV-1 Virions Engineered for Specific Binding to Cell Surface Receptors, MOLECULAR THERAPY, March 2004, 9 (3): 419-427], William F Goins et al. [Retargeting of Herpes Simplex Virus (HSV) Vectors, Curr. Opin. Virol., 2016 Dec. 21:93-101], Xiaodan Wang et al. [Targeted gene transfer to nigrostriatal neurons in the rat brain by helper virus-free HSV-1 vector particles that contain either a chimeric HSV-1 glycoprotein C-GDNF or a gC-BDNF protein, Brain Res. Mol. Brain. Res. 2005 September, 139 (1): 88-102], and the like.

When the cell-targeting domain is inserted and fused into the glycoprotein, a linker peptide may be present at the N-terminus and the C-terminus of the cell-targeting domain. The linker peptide is intended to ensure a distance between the cell-targeting domain and the glycoprotein so that the cell-targeting domain fused to the glycoprotein does not interfere with the formation of the inherent three-dimensional structure thereof due to fusion with the glycoprotein. The linker peptide may be a linker peptide having any length and any sequence, so long as it has the ability to specifically bind to the target molecule of the target cell thereof. Taking into consideration flexibility, solubility, and resistance to proteolysis, the linker preferably comprises at least one amino acid selected from among amino acids such as Ser, Gly, Ala, Thr and the like, and the length thereof may be 1 to 30 amino acids, preferably 3 to 25 amino acids, and more preferably 8 to 20 amino acids.

The recombinant HSV of the present disclosure may be mutated so that non-essential genes that are not required for the propagation of HSV (i.e. survival and replication) are deleted, or so that the function thereof is not exhibited (i.e. transcription or translation is interrupted). Specific examples of the non-essential genes may include a UL3 gene (e.g. GenBank Accession No. AFE62830.1), a UL4 gene (e.g. GenBank Accession No. AFE62831.1), a UL14 gene (e.g. GenBank Accession No. AFE62841.1), a UL16 gene (e.g. GenBank Accession No. AFE62843.1), a UL21 gene (e.g. GenBank Accession No. AFE62848.1), a UL24 gene (e.g. GenBank Accession No. AFE62851.1), a UL31 gene (e.g. GenBank Accession No. AFE62859.1), a UL32 gene (e.g. GenBank Accession No. AFE62860.1), a US3 gene (e.g. GenBank Accession No. AFE62891.1), a UL51 gene (e.g. GenBank Accession No. AFE62880.1), a UL55 gene (e.g. GenBank Accession No. AFE62884.1), a UL56 gene (e.g. GenBank Accession No. AFE62885.1), a US2 gene (e.g. GenBank Accession No. AFE62890.1), a US12 gene (e.g. GenBank Accession No. AFE62901.1; ICP47 gene), a LAT gene (e.g. GenBank Accession No. JQ673480.1), a gB gene (e.g. the sequence between 52996 and 55710 of GenBank Accession No. GU734771.1), a gL gene (e.g. GenBank Accession No. AFE62828.1), a gH gene (e.g. GenBank Accession No. AFE62849.1), a gD gene (e.g. GenBank Accession No. AFE62894.1), and the like.

For more specific information on the non-essential genes of HSV, reference may be made to D. M. Knipe and P. M. Howley (eds.) [Fields Virology (vol. 2) Lippincott Williams & Wilkins, Philadelphia, Pa. 2001. pp. 2399-2460)], Subak-Sharpe J. H. and Dargan D. J. [HSV Molecular Biology: General Aspects of Herpes Simplex Virus Molecular Biology Virus Genes, 1998, 16 (3): 239-251], Travis J. Taylor and David M. Knipe [Proteomics of Herpes Simplex Virus Replication Compartments: Association of Cellular DNA Replication, Repair, Recombination, and Chromatin-Remodeling Proteins with ICP8, J. Virol. 2004 June; 78 (11): 5856-5866], and the like.

The recombinant HSV of the present disclosure may be a recombinant HSV-1 virus, a recombinant HSV-2 virus, or an HSV-1/HSV-2 chimeric virus (i.e. a recombinant HSV in which the genome contains both DNA derived from HSV-1 and DNA derived from HSV-2), preferably a recombinant HSV-1 virus, and more preferably a recombinant HSV-1 derived from an HSV-1 KOS strain. The HSV-1 KOS strain is available from ATCC (Cat No VR-1493TM), and the entire genome sequence of the strain is completely analyzed and represented in GenBank Accession No. JQ673480.1 (Stuart J. Macdonald et al. Genome Sequence of Herpes Simplex Virus 1 Strain KOS. J. Virol. 2012 June; 86 (11): 6371-2).

The genome of the HSV-1 virus is composed of 152 kb double-stranded linear DNA encoding a total of 84 genes comprising two fragments connected to each other, particularly a long fragment (L region) and a short fragment (S region). The long fragment (L region) accounts for about 82% of the genome, and the short fragment (S region) accounts for about 18% of the genome, and the long and short fragments are joined by two IRLs (intermediate inverted repeat sequences), which are junction regions, and a TRL (terminal inverted repeat segment) is present at the end of each fragment. The L region (UL) comprises 56 UL1-UL56 genes and 10 genes (UL8.5, 9.5, 10.5, 12.5, 15.5, 20.5, 26.5, 27.5, 43.5, and 49.5), the S region (US) comprises 12 US1-US12 genes and 2 genes (US1.5 and 8.5), and two IRLs, which are junction regions, comprise 4 genes (ICP4, ICP34.5, ICP0, and LAT).

In the recombinant HSV of the present disclosure, the cell-targeting domain acts to induce the entry of the recombinant HSV of the present disclosure into the target cell by specifically recognizing and binding to the target molecule of the target cell. Here, the target cell is any abnormal cell. In other words, an abnormal cell is a diseased cell that acts as a cause of disease.

The abnormal cell, which is the target cell, is typically a cancer cell. The cancer cell may be any type of carcinoma, such as esophageal cancer, stomach cancer, colorectal cancer, rectal cancer, oral cancer, pharyngeal cancer, laryngeal cancer, lung cancer, colon cancer, breast cancer, uterine cervical cancer, endometrial cancer, ovarian cancer, prostate cancer, testicular cancer, melanoma, bladder cancer, kidney cancer, liver cancer, pancreatic cancer, bone cancer, connective tissue cancer, skin cancer, brain cancer, thyroid cancer, leukemia, Hodgkin's disease, lymphoma, multiple myeloma, blood cancer, and the like.

When the recombinant HSV of the present disclosure targets such a cancer cell as the target cell, the recombinant HSV of the present disclosure acts as an oncolytic virus to destroy cancer cells, thereby exhibiting an anticancer effect.

The target cell targeted by the recombinant HSV of the present disclosure may be any diseased cell for gene therapy, in addition to the cancer cell. Here, the diseased cell for gene therapy is a cell which has an abnormal gene that causes a disease or in which a certain gene is expressed or functions abnormally, and a genetic material such as a normal gene corresponding to the abnormal gene is transferred to the abnormal cell by the recombinant HSV of the present disclosure such that the abnormal gene or the like is expressed or functions normally, thereby leading to the treatment of the corresponding disease.

Such a disease may be Alzheimer's disease, amyotrophic lateral sclerosis (ALS), Lou Gehrig's disease, osteoarthritis, atherosclerosis, Charcot-Marie-Tooth disease (CMT), chronic obstructive pulmonary disease (COPD), chronic traumatic encephalopathy, diabetes, Ehlers-Danlos syndrome, essential tremor, Friedreich's ataxia, Huntington's disease, inflammatory bowel disease (IBD), keratoconus, keratoglobus, macular degeneration, Marfan syndrome, multiple sclerosis, multiple system atrophy, muscular dystrophy, Niemann Pick disease, osteoporosis, Parkinson's disease, progressive supranuclear palsy, prostatitis, retinitis pigmentosa, rheumatoid arthritis, or Tay-Sachs disease.

When the recombinant HSV of the present disclosure targets such a diseased cell for gene therapy, the recombinant HSV of the present disclosure is used after elimination of the cell-lytic capability thereof by inactivating a gene that is essential for propagation thereof, for example, an ICP27 gene, an ICP4 gene, or the like.

In the recombinant HSV of the present disclosure, a target molecule of a target cell that is specifically recognized and bound by the cell-targeting domain is any antigen or any receptor present on the surface of a diseased cell, which is an abnormal cell.

In particular, the recombinant HSV of the present disclosure may be useful as an oncolytic virus for anticancer therapy. Here, the target molecule is any antigen or any receptor present on the surface of the cancer cell. The target molecule, that is, the antigen or receptor of a cancer cell, is preferably an antigen or receptor that is expressed only in cancer cells or is overexpressed in cancer cells compared to normal cells.

Examples of the antigen or receptor on the surface of cancer cells may include target molecules, such as EGFRvIII (epidermal growth factor receptor variant III) expressed in glioblastoma, EGFR (epidermal growth factor receptor) overexpressed in anaplastic thyroid cancer, breast cancer, lung cancer, glioma and the like, a metastin receptor overexpressed in papillary thyroid cancer and the like, an ErbB-based receptor tyrosine kinase overexpressed in breast cancer and the like, HER2 (human epidermal growth factor receptor 2) overexpressed in breast cancer, bladder cancer, gallbladder cancer, cholangiocarcinoma, esophagogastric junction cancer and the like, a tyrosine kinase-18-receptor (c-Kit) overexpressed in sarcomatoid renal carcinoma and the like, an HGF receptor c-Met overexpressed in esophageal adenocarcinoma and the like, CXCR4 or CCR7 overexpressed in breast cancer and the like, an endothelin-A receptor overexpressed in prostate cancer, PPAR-δ (peroxisome proliferator activated receptor δ) overexpressed in rectal cancer and the like, PDGFR-α (platelet-derived growth factor receptor α) overexpressed in ovarian cancer and the like, CD133 overexpressed in liver cancer, multiple myeloma and the like, CEA (carcinoembryonic antigen) overexpressed in lung cancer, colorectal cancer, stomach cancer, pancreatic cancer, breast cancer, rectal cancer, colon cancer, medullary thyroid cancer and the like, EpCAM (epithelial cell adhesion molecule) overexpressed in liver cancer, stomach cancer, colorectal cancer, pancreatic cancer, breast cancer and the like, MSLN (mesothelin) overexpressed in lung cancer, breast cancer, pancreatic cancer, ovarian cancer and the like, GD2 (disialoganglioside) overexpressed in neuroblastoma and the like, GPC3 (glypican 3) overexpressed in hepatocellular carcinoma and the like, PSMA (prostate-specific membrane antigen) overexpressed in prostate cancer and the like, TAG-72 (tumor-associated glycoprotein 72) overexpressed in ovarian cancer, breast cancer, colon cancer, lung cancer, pancreatic cancer and the like, GD3 (disialoganglioside) overexpressed in melanoma and the like, HLA-DR (human leukocyte antigen-DR) overexpressed in blood cancer, solid cancer and the like, MUC1 (Mucin 1) overexpressed in advanced solid cancer and the like, NY-ESO-1 (New York esophageal squamous cell carcinoma 1) overexpressed in advanced non-small-cell lung cancer and the like, LMP1 (latent membrane protein 1)

overexpressed in nasopharyngeal neoplasms and the like, TRAILR2 (tumor-necrosis factor-related apoptosis-inducing ligand receptor) overexpressed in lung cancer, non-Hodgkin's lymphoma, ovarian cancer, colon cancer, colorectal cancer, pancreatic cancer and the like, VEGFR2 (vascular endothelial growth factor receptor 2) as an angiogenesis factor receptor, and HGFR (hepatocyte growth factor receptor) overexpressed in hepatocellular carcinoma and the like. Moreover, the surface antigen of cancer stem cells, such as CD44, CD166 or the like, may be a target molecule. Many target molecules overexpressed in cancer cells compared to normal cells are known in the art, and for other target molecules in addition to the examples listed above, reference may be made to Anne T. Collins et al. [Prospective Identification of Tumorigenic Prostate Cancer Stem Cells. Cancer Res. 2005 Dec. 1; 65 (23): 10946-51], Chenwei Li et al. [Identification of Pancreatic Cancer Stem Cells. Cancer Res. 2007 Feb. 1; 67 (3): 1030-7], Shuo Ma et al. [Current Progress in CAR-T Cell Therapy for Solid Tumors. Int. J. Biol. Sci. 2019 Sep. 7; 15 (12): 2548-2560], Dhaval S. Sanchala et al. [Oncolytic Herpes Simplex Viral Therapy: A Stride Toward Selective Targeting of Cancer Cells. Front Pharmacol. 2017 May 16; 8:270], and the like.

In particular, the target molecule is preferably HER2, EpCAM or CEA in the present disclosure.

In the present disclosure, the cell-targeting domain may be an antibody derivative or an antibody analogue, in addition to a complete antibody having the ability to specifically bind to the target molecule. The antibody derivative is a fragment of a complete antibody that includes at least one antibody variable region having the ability to specifically bind to the target molecule, or is a modified antibody. Examples of the antibody derivative may include antibody fragments such as Fab, scFv, Fv, VhH, VH, VL, etc., multivalent or multispecific modified antibodies such as Fab2, Fab3, minibodies, diabodies, tribodies, tetrabodies, bis-scFv, etc., and the like. The antibody analogue is an artificial peptide or polypeptide that has the ability to specifically bind to the target molecule, like the antibody, but is different in structure from the antibody, and generally has a lower molecular weight than the antibody. Examples of the antibody analogue may include ABD, Adhiron, affibodies, affilins, affimers, alphabodies, anticalin, armadillo repeat protein, centyrins, DARPins, fynomers, a Kunitz region, ProNectin, repebodies, and the like.

A considerably large number of documents in the art regarding the antibody, antibody derivative, antibody analogue, and production thereof have been published, and examples thereof include Renate Kunert & David Reinhart [Advances in recombinant antibody manufacturing. Appl. Microbiol. Biotechnol. 2016 April; 100 (8): 3451-61], Holliger P. and Hudson P. J. [Engineered antibody fragments and the rise of single domains, Nat. Biotechnol. 2005 September; 23 (9): 1126-36], Xiaowen Yu et al. [Beyond Antibodies as Binding Partners: The Role of Antibody Mimetics in Bioanalysis, Annual Review of Analytical Chemistry, 2017, 10:293-320], Abdul Rasheed Baloch et al. [Antibody mimetics: promising complementary agents to animal-sourced antibodies, Critical Reviews in Biotechnology, 2016, 36:268-275], and the like.

In the present disclosure, the cell-targeting domain may be a natural polypeptide ligand, as well as the complete antibody for a target molecule, the antibody derivative, or the antibody analogue. The natural polypeptide ligand is a ligand in which the receptor of the target cell to which the ligand specifically binds is a target molecule, and examples of such a ligand may include cytokines, chemokines, growth factors, and the like, and particularly EPO (erythropoietin), EGF (epidermal growth factor), IL-13, and the like.

In the present disclosure, the cell-targeting domain is preferably an scFv (single-chain variable fragment). The scFv is a single-chain antibody in which the heavy-chain variable region (VH) and the light-chain variable region (VL) of an immunoglobulin are linked via a short linker peptide. In the scFv, the C-terminus of VH is linked to the N-terminus of VL, or the C-terminus of VL is linked to the N-terminus of VH. In the scFv, the linker peptide may be a linker peptide having any length and any sequence, so long as it does not interfere with the inherent three-dimensional structures of heavy and light chains and enables the heavy and light chains to be spatially adjacent to each other to thus have the ability to specifically bind to the target molecule. Taking into consideration flexibility, solubility, resistance to proteolysis, etc., the linker preferably comprises at least one amino acid selected from among amino acids such as Ser, Gly, Ala, Thr, etc., and the length thereof may be 1-30 amino acids, preferably 3-25 amino acids, and more preferably 8-20 amino acids.

In the present disclosure, the target molecule targeted by scFv is HER2, EpCAM or CEA. Specifically, scFv for HER2 is preferably configured such that VH of SEQ ID NO: 4 and VL of SEQ ID NO: 5 are linked in the order of VH, linker peptide and VL via a linker peptide (i.e. the C-terminus of VH is linked to the N-terminus of VL via the linker peptide), and scFv for EpCAM is preferably configured such that VL of SEQ ID NO: 6 and VH of SEQ ID NO: 7 are linked in the order of VL, linker peptide and VH via a linker peptide (i.e. the C-terminus of VL is linked to the N-terminus of VH via the linker peptide). Also, scFV for CEA is preferably configured such that VL of SEQ ID NO: 8 and VH of SEQ ID NO: 9 are linked in the order of VL, linker peptide and VH via a linker peptide (i.e. the C-terminus of VL is linked to the N-terminus of VH via the linker peptide).

In the present disclosure, in order to facilitate cloning, an amino acid corresponding to an arbitrary restriction enzyme site may be interposed at the site adjacent to the VH and VL of scFv and the glycoprotein when scFv for the cell target molecule is used as the cell-targeting domain, between VH and VL of scFv, or between VH or VL and the linker peptide when the linker peptide is disposed between VH and VL of scFv. For example, EF (base sequence: GAATTC), on which the restriction enzyme EcoRI acts, or GS (base sequence: GGATCC), on which BamHI acts, may be interposed therebetween.

In the present disclosure, when the recombinant HSV is used as an oncolytic virus for anticancer therapy, in order to express factors alone or in any combination for inducing or enhancing an immune response to cancer cells, the recombinant HSV may be configured such that a gene for the corresponding factor is inserted into the HSV genome. Such factors may be manipulated so as to express cytokines, chemokines, immune checkpoint antagonists (e.g. antibodies, antibody derivatives or antibody analogues, especially scFv), co-stimulatory factors capable of inducing activation of immune cells (T cells or NK cells), antagonists capable of inhibiting the function of TGFβ, which suppresses the immune response to cancer cells (e.g. antibodies, antibody derivatives or antibody analogues, especially scFv), heparanase capable of degrading heparan sulfate proteoglycan for a solid tumor microenvironment, antagonists capable of inhibiting the function of angiogenesis factor receptor VEGFR-2 (VEGF receptor-2) (e.g. antibodies, antibody derivatives or antibody analogues, especially scFv), and the like.

As cytokines, for example, interleukins such as IL-2, IL-4, IL-7, IL-10, IL-12, IL-15, IL-18, IL-24, etc., interferons such as IFNα, IFNβ, IFNγ, etc., tumor necrosis factors such as TNFα, etc., and colony-stimulating factors such as GM-CSF, G-CSF, FLT3L, etc. may be used alone or in any combination of two or more thereof so as to be expressed in the recombinant HSV.

As chemokines, for example, CCL2 (C-C motif chemokine ligand 2), CCL5 (RANTES), CCL7, CCL9, CCL10, CCL12, CCL15, CCL19, CCL21, CCL20, and XCL-1 (X-C motif chemokine ligand 1) may be used alone or in combination so as to be expressed in the recombinant HSV.

As immune checkpoint antibodies, antagonists to PD-1 (programmed cell death 1), PD-L1 (programmed cell death ligand 1), PD-L2 (programmed cell death ligand 2), CD27 (cluster of differentiation 27), CD28 (cluster of differentiation 28), CD70 (cluster of differentiation 70), CD80 (cluster of differentiation 80), CD86 (cluster of differentiation 86), CD137 (cluster of differentiation 137), CD276 (cluster of differentiation 276), KIR (killer-cell immunoglobulin-like receptor), LAG3 (lymphocyte activation gene 3), GITR (glucocorticoid-induced TNFR-related protein), GITRL (glucocorticoid-induced TNFR-related protein ligand), and CTLA-4 (cytolytic T lymphocyte associated antigen-4) may be used alone or in combination so as to be expressed in the recombinant HSV.

As co-stimulatory factors, CD2, CD7, LIGHT, NKG2C, CD27, CD28, 4-1BB, OX40, CD30, CD40, LFA-1 (lymphocyte function-associated antigen-1), ICOS (inducible T cell co-stimulator), CD3γ, CD3δ, and CD3ε may be used alone or in combination so as to be expressed in the recombinant HSV.

In the present disclosure, the recombinant HSV may be manipulated so as to express a prodrug-activating enzyme that converts a prodrug into a drug that exhibits toxicity to cancer cells. Examples of the prodrug-activating enzyme may include cytosine deaminase, which converts 5-FC (5-fluorocytosine) as a prodrug into 5-FU (5-fluorouracil) as a drug, rat cytochrome P450 (CYP2B1), which converts CPA (cyclophosphamide) as a prodrug into PM (phosphoramide mustard) as a drug, carboxylesterase, which converts irinotecan (SN-38150) as a prodrug into SN-38 as a drug, bacterial nitroreductase, which converts BC1954 as a prodrug into 4-hydroxylamine151 as a DNA cross-linker, PNP (purine nucleoside phosphorylase) isolated from *E. coli*, which converts 6-methylpurine-2'-deoxyriboside as a prodrug into 6-methylpurine as a drug, and the like.

Moreover, in the present disclosure, the recombinant HSV may be manipulated so as to express TRAIL (TNF-related apoptosis-inducing ligand). TRAIL is known to induce the death of cancer cells by binding to the receptor thereof, which is overexpressed in cancer cells (Kaoru Tamura et al. Multimechanistic Tumor Targeted Oncolytic Virus Overcomes Resistance in Brain Tumors. Mol. Ther. 2013 January; 21 (1): 68-77).

For more details regarding the use of factors or prodrug-activating enzymes for inducing or enhancing these immune responses, reference may be made to Michele Ardolino et al. [Cytokine treatment in cancer immunotherapy, J. Oncotarget, Oncotarget. 2015 Aug. 14; 6 (23):], Bernhard Homey et al. [Chemokines: Agents for the Immunotherapy of Cancer. Nat. Rev. Immunol. 2002 March; 2 (3): 175-84], Marianela Candolfi et al. [Evaluation of proapoptotic transgenes to use in combination with Flt3L in an immune-stimulatory gene therapy approach for Glioblastoma multiforme (GBM), J. FASEB J., 2008, 22:107713], Danny N Khalil et al. [The Future of Cancer Treatment: Immunomodulation, CARs and Combination Immunotherapy. Nat. Rev. Clin. Oncol. 2016 May; 13 (5): 273-90], Paul E. Hughes et al. [Targeted Therapy and Checkpoint Immunotherapy Combinations for the Treatment of Cancer. Trends Immunol. 2016 July; 37 (7): 462-476], Cole Peters and Samuel D. Rabkin [Designing herpes viruses as oncolytics, Mol. The Oncolytics. 2015; 2:15010], and the like.

In the present disclosure, the factors or prodrug-activating enzymes for inducing or enhancing immune responses are configured such that the expression cassette of the gene thereof (i.e. a construct in which the gene thereof is operably linked with a promoter sequence that enables expression thereof and a polyadenylation signal sequence) is inserted into the HSV genome without inhibiting the propagation of HSV. Such insertion may be performed without deletion of the HSV genome, or insertion into loci from which some or all non-essential genes in the HSV genome are deleted may be conducted. Here, upon insertion without deletion of the HSV genome, insertion may be performed between genes, and preferred insertion loci are, for example, between UL3 and UL4, between UL26 and UL27, between UL37 and UL38, between UL48 and UL49, between UL53 and UL54, and between US1 and US2. Upon insertion into loci from which non-essential genes are deleted or into genes without deletion of non-essential genes, such non-essential genes may be selected from among any non-essential genes, as described above.

In the present disclosure, the gene-expressing cassette of the factor for inducing or enhancing the above immune response is configured such that the target gene thereof is operably linked with a promoter sequence that enables expression thereof and a polyadenylation signal sequence, which is a transcription termination signal sequence. Here, “operably linked” means linkage that enables transcription and/or translation of the expressed target gene. For example, when any promoter affects the transcription of the target gene linked thereto, the promoter is said to be operably linked to the target gene.

Typically, a promoter is a nucleic acid sequence having a function of controlling transcription of one or more genes, is located at the upstream (5' side) of the transcription start site of a gene, and includes a site for binding to a DNA-dependent RNA polymerase, a transcription start site, a transcription-factor-binding site, and the like. In the case of eukaryotic origin, the promoter includes a TATA box upstream of the transcription start site (usually located at positions −20 to −30 with respect to the transcription start site (+1)), a CAAT box (usually located at position −75 with respect to the transcription start site), an enhancer, a transcription-factor-binding site, and the like.

So long as the promoter is able to express a target gene linked thereto, all of a constitutive promoter (which induces gene expression at all times), an inducible promoter (which induces expression of a target gene in response to a specific external stimulus), a tissue-specific promoter (which induces gene expression in specific tissues or cells), a tissue-non-specific promoter (which induces gene expression in all tissues or cells), an endogenous promoter (which is derived from virus-infected cells), and an exogenous promoter (which is derived from cells other than virus-infected cells) may be used. Many promoters are known in the art, and an appropriate promoter may be selected therefrom and used. For example, useful are a CMV (cytomegalovirus) promoter, a RSV (Rous sarcoma virus) promoter, an HSV (herpes simplex virus) TK (thymidine kinase) promoter, an adenovirus late promoter, a vaccinia virus 75K promoter, an SV40 promoter, a metallothionein promoter, a CD45 promoter (hematopoietic-stem-cell-specific promoter), a CD14 promoter (monocyte-specific promoter), and a cancer-cell-specific promoter (tumor-specific promoter) such as Survivin, Midkine, TERT, CXCR4, etc. In particular, when a cancer-cell-specific promoter is used, the expression of the target gene is induced only in the cancer cells, thus suppressing the expression of the target gene in normal cells, thereby increasing the safety of the recombinant HSV of the present disclosure.

The expression cassette is configured to include a transcription termination signal sequence in addition to the promoter, and the transcription termination signal sequence is a sequence that acts as a poly(A) addition signal (polyadenylation signal) to increase the integrity and efficiency of transcription. Many transcription termination signal sequences are known in the art, and an appropriate sequence, such as an SV40 transcription termination signal sequence, an HSV TK (herpes simplex virus thymidine kinase) transcription termination signal sequence, or the like, may be selected therefrom and used.

Another aspect of the present disclosure pertains to a pharmaceutical composition for treating cancer containing the recombinant HSV described above as an active ingredient.

The pharmaceutical composition of the present disclosure has anticancer effects against a carcinoma expressing a target molecule to which the cell-targeting domain, inserted and fused into the gH of the recombinant HSV of the present disclosure, specifically binds. Examples of the carcinoma are as described above in relation to the target molecule.

In particular, it is preferable that the composition of the present disclosure have anticancer effects against carcinoma having tumor cells expressing HER2, EpCAM or CEA. Examples of tumor cells expressing HER2 include breast cancer cells, ovarian cancer cells, stomach cancer cells, lung cancer cells, head and neck cancer cells, osteosarcoma cells, glioblastoma multiforme cells, salivary gland tumor cells, and the like. Also, examples of tumor cells expressing EpCAM include liver cancer cells, prostate cancer cells, breast cancer cells, colorectal cancer cells, lung cancer cells, gallbladder cancer cells, pancreatic cancer cells, stomach cancer cells, and the like. Also, examples of tumor cells expressing CEA include colorectal cancer cells, stomach cancer cells, lung cancer cells, breast cancer cells, rectal cancer cells, colon cancer cells, liver cancer cells, and the like.

In the present disclosure, anticancer effects include death of cancer cells, decreased viability of cancer cells, inhibition or delay of pathological symptoms of cancer due to suppression of cancer-cell propagation, inhibition or delay of onset of such pathological symptoms, inhibition of cancer metastasis, and inhibition of cancer recurrence.

Moreover, the pharmaceutical composition of the present disclosure may be used in combination with or in a mixture with an approved anticancer agent. Examples of the anticancer agent may include any anticancer agents, any cytokine drugs, any antibody drugs, any immune checkpoint inhibitor drugs, and any cell therapeutic agents (for car-T cell therapy or car-NK cell therapy) that exhibit cytotoxicity to cancer cells, such as metabolic antagonists, alkylating agents, topoisomerase antagonists, microtubule antagonists, and plant-derived alkaloids. Specific examples thereof may include taxol, nitrogen mustard, imatinib, oxaliplatin, gefitinib, bortezomib, sunitinib, carboplatin, cisplatin, rituximab, erlotinib, sorafenib, IL-2 drug, IFN-α drug, IFN-γ drug, trastuzumab, blinatumomab, ipilimumab, pembrolizumab, nivolumab, atezolizumab, durvalumab, bevacizumab, cetuximab, tisagenlecleucel (Kymriah), axicabtagene ciloleucel (Yescarta), and the like. In addition to the exemplary anticancer agents, other anticancer agents known in the art may be used without limitation in combination with or in a mixture with the pharmaceutical composition of the present disclosure.

The pharmaceutical composition of the present disclosure may include a pharmaceutically acceptable carrier or excipient, and may thus be prepared in the form of an oral formulation or a parenteral formulation through a typical method known in the art depending on the route of administration.

Such a pharmaceutically acceptable carrier or excipient does not impair the activity or properties of the drug and is not itself toxic to the human body, and examples thereof may include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water (e.g. saline and sterile water), syrup, methyl cellulose, methylhydroxybenzoate, propylhydroxybenzoate, talc, magnesium stearate, mineral oil, Ringer's solution, buffer, maltodextrin solution, glycerol, ethanol, dextran, albumin, and any combination thereof. In particular, when the pharmaceutical composition of the present disclosure is formulated in the form of a liquid solution, an appropriate carrier or excipient may include saline, sterile water, Ringer's solution, buffered saline, albumin injection solution, dextrose solution, maltodextrin solution, glycerol, and ethanol, which may be used alone or in combination. If necessary, other typical pharmaceutical additives, such as antioxidants, buffers, bacteriostatic agents, etc., may be added and used.

When the pharmaceutical composition of the present disclosure is prepared into an oral formulation, it may be manufactured in the form of a tablet, troche, capsule, elixir, suspension, syrup, wafer, etc., and when prepared into a parenteral formulation, especially an injection, it may be manufactured in a unit dose ampoule or a multi-dose form. The pharmaceutical composition of the present disclosure may also be manufactured in the form of a solution, suspension, tablet, pill, capsule, sustained-release formulation, and the like.

The pharmaceutical composition of the present disclosure may be formulated in a unit dosage form suitable for administration to a patient's body according to a typical method in the pharmaceutical field, and may be administered through an oral route of administration or a parenteral route of administration, such as dermal, intralesional, intravenous, intramuscular, intraarterial, intramedullary, intrathecal, intraventricular, pulmonary, transdermal, subcutaneous, intraperitoneal, intranasal, enteral, topical, sublingual, intravaginal, and rectal routes, using any administration method commonly used in the art.

The dose (effective amount) of the pharmaceutical composition of the present disclosure may vary depending on factors such as the formulation method, the administration mode, the patient's age, weight and gender, pathological conditions, diet, administration time, administration route, excretion rate, and response sensitivity, and may be appropriately determined by those skilled in the art in consideration of these factors. In a preferred embodiment, the pharmaceutical composition of the present disclosure is prepared as an injection in a unit dosage form. When prepared as an injection in a unit dosage form, the amount of the recombinant HSV included per unit dose of the pharmaceutical composition of the present disclosure may range from $10^2$-$10^{14}$ pfu, particularly $10^4$-$10^{11}$ pfu.

Still another aspect of the present disclosure pertains to a method of treating or preventing cancer (tumors), including administering the pharmaceutical composition containing the recombinant HSV described above to a subject such as a patient in an effective amount.

The method of treating cancer is made possible by lysing and killing cancer cells having a target molecule to which the cell-targeting domain inserted and fused into the gH of the recombinant HSV of the present disclosure specifically binds. Therefore, the treatment method of the present disclosure may be applied to any carcinoma having such a target molecule. In particular, the treatment method of the present disclosure is preferably applied to a carcinoma expressing HER2, EpCAM, or CEA.

The treatment method of the present disclosure may be used without limitation in combination with the other cancer treatment methods described above. For example, cytotoxic anticancer agents, cytokine drugs, antibody drugs, immune checkpoint inhibitor drugs, cell therapeutic agents (for car-T cell therapy or car-NK cell therapy), radiotherapy, surgery, etc., as exemplified above, may be used before or after administration of the pharmaceutical composition of the present disclosure or in a manner of simultaneous administration in combination with the pharmaceutical composition of the present disclosure.

In the treatment method of the present disclosure, the effective amount is an amount in which the pharmaceutical composition of the present disclosure is administered so as to exhibit the intended medical effect, such as a cancer treatment or prevention effect, when the pharmaceutical composition of the present disclosure is administered to a subject such as a patient for the administration period based on the recommendation of a medical expert, etc. As described above, such an effective amount may be appropriately determined by a person skilled in the art, such as a medical expert, etc., depending on the patient's age, weight and gender, pathological conditions, and the like, as described above.

In the treatment method of the present disclosure, the pharmaceutical composition is preferably administered in the form of an injection to a patient or the like in a mode of parenteral administration, for example, intralesional (intratumoral), intravenous, intramuscular or intraarterial administration or the like.

Advantageous Effects

According to the present disclosure, it is possible to provide a recombinant HSV having a modified glycoprotein gH for retargeting and the use thereof.

The recombinant HSV of the present disclosure is capable of infecting a target cell having a target molecule to which a cell-targeting domain specifically recognizes and binds due to the presence of the cell-targeting domain in the glycoprotein gH thereof, and is thus useful for anticancer therapy or gene therapy.

DETAILED DESCRIPTION

A better understanding of the present disclosure will be given through the following examples. However, these examples are not to be construed as limiting the scope of the present disclosure.

<Example 1> Production of HVEM-Restricted HSV-1 Virus

Figure 1:
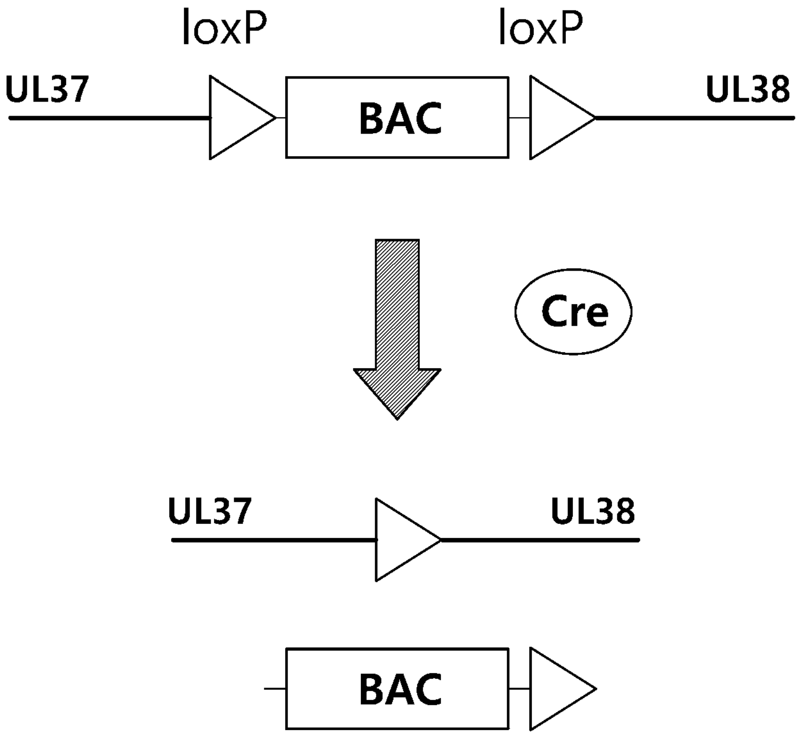
FIG. 1 schematically shows the genomic structure of KOS-37 BAC.

An HSV-1 gene is composed of a large gene about 152 kb in size, and thus KOS-37/BAC (GenBank Accession No. MF156583) (Gierasch W. W. et al., Construction and characterization of bacterial artificial chromosomes containing HSV-1 strains 17 and KOS, J. Virol. Methods. 2006. 135: 197-206) was used to insert a foreign gene or a mutation at a specific locus. The HSV-1 KOS strain is a kind of HSV-1 strain mainly used in laboratories because of the well-known characteristics thereof and the usefulness thereof for investigation of gene function and etiology (Smith K O. Proc. Soc. Exp. Biol. Med. 1964. 115:814-816). KOS-37/BAC, manufactured by inserting a BAC plasmid into a KOS genome, enables cloning at the bacterial level through transformation of DH10B bacteria (Invitrogen) (Gierasch W. W. et al., Construction and characterization of bacterial artificial chromosomes containing HSV-1 strains 17 and KOS, J. Virol. Methods. 2006. 135:197-206). In the KOS-37/BAC, BAC (bacterial artificial chromosome) is inserted along with a LoxP site at both sides thereof into a locus between UL37 and UL38 of the HSV-1 KOS genome. This is intended to remove the BAC gene using a Cre-Lox system in subsequent procedures. The schematic view thereof is shown in FIG. 1.

In order to manufacture HVEM-restricted HSV-1, which enters cells only through the HVEM cell receptor, a gD-R222N/F223I HSV-1 virus, in which arginine (R) at position 222 and phenylalanine (F) at position 223 of the HSV-1 gD amino acid sequence (GenBank Accession No. ASM47818, SEQ ID NO: 10) were substituted with asparagine (N) and isoleucine (I), respectively, was manufactured.

The gD-R222N/F223I HSV-1 virus manufactured through mutation is able to infect host cells only through HVEM (HveA) rather than nectin-1 as the cell entry receptor (Uchida H. et al., Generation of herpesvirus entry mediator (HVEM)-restricted herpes simplex virus type 1 mutant viruses: resistance of HVEM-expressing cells and identification of mutations that rescue nectin-1 recognition, J. Virol. 2009. 83 (7): 2951-2961), and is thus advantageous from the aspect of safety because it cannot infect normal cells having the nectin-1 receptor.

Figure 2:
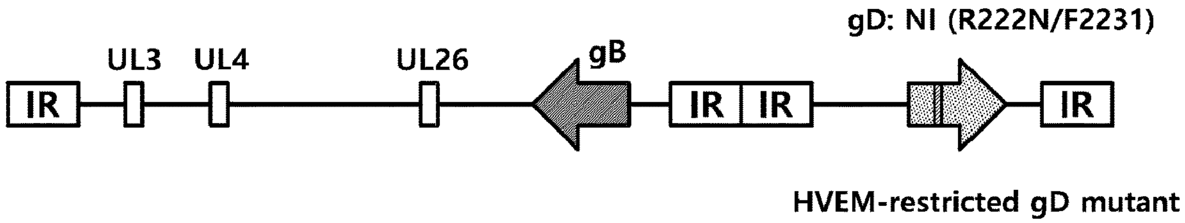
FIG. 2 schematically shows the genomic structure of an HVEM-restricted HSV-1 virus.

The genomic structure of the HVEM-restricted KOS-gD-R222N/F223I virus is schematically shown in FIG. 2.

The KOS-gD-R222N/F223I HSV-1 virus was manufactured by introducing R222N/F223I mutations into the gD site of KOS-37/BAC according to the manufacturer's protocol using a counter-selection BAC modification kit (GeneBridges Inc.).

Specifically, an *E. coli* clone containing KOS-37/BAC was transformed with a pRed/ET plasmid expressing RecE and RecT capable of performing the function of homologous recombination (Muyrers J. P. et al., Rapid modification of bacterial artificial chromosomes by ET-recombination, Nucleic Acids Res. 1999. 27 (6): 1555-1557). A gD-rpsL-neo/kan cassette was manufactured using a set of homologous region primers (forward primer gD-rpsL For: SEQ ID NO: 11, reverse primer gD-rpsL Rev: SEQ ID NO: 12) including a locus at which to introduce a mutation into gD. The gD-rpsL-neo/kan cassette is composed of the gD homologous region at the insertion locus, the rpsL gene, which is a selective marker for conferring sensitivity to streptomycin, and the neo/kan gene, which confers kanamycin resistance. When the gD-rpsL-neo/kan cassette is inserted, *E. coli* having sensitivity to streptomycin antibiotics due to the rpsL gene and kanamycin resistance due to the neo/kan gene is manufactured. After inducing the expression of RecE and RecT so as to enable homologous recombination by activating the function of pRed/ET by adding L-arabinose (Sigma-Aldrich) to the *E. coli* clone containing KOS-37/BAC and pRed/ET (Muyrers J. P. et al., Rapid modification of bacterial artificial chromosomes by ET-recombination, Nucleic Acids Res. 1999. 27 (6): 1555-1557), transformation with 200 ng of the manufactured gD-rpsL-neo/kan cassette was performed. Through homologous recombination, the gD-rpsL-neo/kan cassette is inserted into the gD locus of KOS-37/BAC. *E. coli* in which gD-rpsL-neo/kan is inserted into KOS-37/BAC exhibits kanamycin resistance, but streptomycin resistance is blocked by the rpsL gene. It was inferred for *E. coli* obtained from the kanamycin medium that gD-rpsL-neo/kan was inserted therein, and the final step of inserting a gene was performed. After inducing the expression of RecE and RecT so as to enable homologous recombination by activating the function of pRed/ET by adding L-arabinose (Sigma-Aldrich) to *E. coli* containing the KOS 37-BAC gD-rpsL-neo/kan clone, transformation with 100 pmol of R222N_F223I_mutant (SEQ ID NO: 13), which is an oligonucleotide in which R and F at respective positions 222 and 223 of gD were substituted with N and I, was performed. Based on the principle whereby streptomycin resistance blocked by rpsL is activated upon replacing the existing gD-rpsL-neo/kan cassette with the inserted oligonucleotide, candidates were selected in a streptomycin medium (Heermann R. et al., Simple generation of site-directed point mutations in the *Escherichia coli* chromosome using Red®/ET® Recombination. Microb. Cell Fact. 7, 14, 2008). DNA was isolated from the selected candidates using a DNA preparation method (Horsburgh B. C. et al., Genetic manipulation of herpes simplex virus using bacterial artificial chromosomes, Methods Enzymol. 1999. 306:337-352), and the substitution of N and I at respective positions 222 and 223 of gD was confirmed through PCR (polymerase chain reaction) and DNA sequencing.

Next, for viral production, the completed KOS-37/BAC-gD-R222N/F223I DNA was extracted using a large-construct DNA purification kit (Macherey-Nagel), after which $2\times10^5$ Cre-Vero-HVEM cells were transfected with 1 μg of DNA using a Lipofectamine 2000 reagent (Invitrogen). Then, cell culture was carried out using DMEM (Dulbecco's Modified Eagle's Medium) (Welgene) containing 100 U/ml penicillin/100 μg/ml streptomycin (Welgene) and 10% FBS (fetal bovine serum, Welgene). The Cre-Vero-HVEM cell line is a cell line inducing HVEM protein expression by inserting the HVEM gene into the Cre-Vero cell line (Gierasch W. W. et al., Construction and characterization of bacterial artificial chromosomes containing HSV-1 strains 17 and KOS, J. Virol. Methods. 2006. 135:197-206). The reason for using Cre-Vero-HVEM is that the BAC gene of KOS-37/BAC-gD-R222N/F223I may be removed using Cre recombinase of the cells and also that infection with the KOS-gD-R222N/F223I virus due to HVEM overexpression is effective, and thus mass production of viruses becomes easy. 3-4 days after gene introduction, the formation of cell plaques was confirmed, after which the virus-containing cells were collected, subjected three times to a freeze-thaw process (Gierasch W. W. et al., Construction and characterization of bacterial artificial chromosomes containing HSV-1 strains 17 and KOS, J. Virol. Methods. 2006. 135: 197-206), and sonicated, ultimately obtaining a KOS-gD-R222N/F223I virus.

<Example 2> Production of HVEM-Restricted HSV-1 Virus Expressing EmGFP

For the production of HVEM-restricted HSV-1 expressing EmGFP, an expression cassette capable of expressing EmGFP (emerald green fluorescent protein) was inserted into the UL26/UL27 locus of the KOS-37/BAC-gD-R222N/F223I DNA manufactured in Example 1 (Tiffany A. et al., Engineering herpes simplex viruses by infection-transfection methods including recombination site targeting by CRISPR/Cas9 nucleases, J. Virol. Methods. 2015. 231:18-25). This is to facilitate the observation of viral production and infection using EmGFP as a marker. A pCDNA6.2-GW/EmGFP-miR plasmid (Invitrogen) was used to manufacture the EmGFP cassette.

Figure 3:
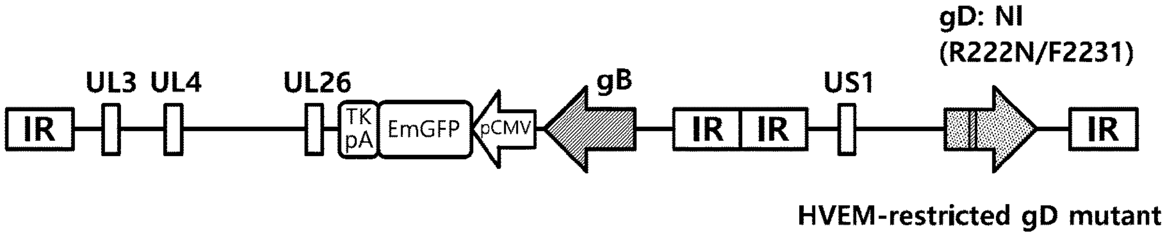
FIG. 3 schematically shows the genomic structure of an HVEM-restricted HSV-1 virus expressing EmGFP.

The genomic structure of KOS-EmGFP-gD-R222N/F223I expressing EmGFP is schematically shown in FIG. 3.

For EmGFP expression, pCMV-EmGFP-tkpA using pCMV as a gene promoter of cytomegalovirus and tkpA as a polyadenylation signal of HSV TK (herpes simplex virus thymidine kinase) was inserted into KOS-37/BAC-gD-R222N/F223I DNA.

All insertion methods were carried out according to the manufacturer's protocol using a counter-selection BAC modification kit (GeneBridges Inc.), as in Example 1.

Specifically, a clone containing KOS-37/BAC-gD-R222N/F223I was transformed with a pRed/ET plasmid expressing RecE and RecT capable of performing the function of homologous recombination (Muyrers J. P. et al., Rapid modification of bacterial artificial chromosomes by ET-recombination, Nucleic Acids Res. 1999. 27 (6): 1555-1557). A UL26/27-rpsL-neo/kan cassette was manufactured using a set of homologous region primers (forward primer UL26/27-rpsL_For: SEQ ID NO: 14, reverse primer UL26/27-rpsL_Rev: SEQ ID NO: 15) including a locus at which to introduce a target gene between UL26 and UL27. The clone containing KOS-37/BAC-gD-R222N/F223I DNA and pRed/ET was added with L-arabinose (Sigma-Aldrich) to thus induce homologous recombination, followed by transformation with 200 ng of the manufactured UL26/27-rpsL-neo/kan cassette. The UL26/27-rpsL-neo/kan cassette is inserted into the UL26/27 locus of KOS-37/BAC through homologous recombination. *E. coli* into which UL26/27-rpsL-neo/kan is inserted exhibits kanamycin resistance, but streptomycin resistance is blocked by the rpsL gene. It was inferred for *E. coli* obtained from the kanamycin medium that UL26/27-rpsL-neo/kan was inserted therein, and the final step of inserting a gene was performed.

*E. coli* containing the UL26/27-rpsL-neo/kan cassette was added with L-arabinose (Sigma-Aldrich) activating the function of pRed/ET to thus induce homologous recombination, followed by transformation with 200 ng of a UL26/27-tkpA-EmGFP-pCMV cassette. The UL26/27-tkpA-EmGFP-pCMV cassette was manufactured using a pCDNA6.2-GW/EmGFP-miR plasmid (Invitrogen) as a template, a forward primer UL26/27-tkpA_For (SEQ ID NO: 16), and a reverse primer UL26/27-pCMV_Rev (SEQ ID NO: 17).

Based on the principle whereby streptomycin resistance blocked by rpsL is activated upon replacing the existing UL26/27-rpsL-neo/kan cassette with the inserted UL26/27-tkpA-EmGFP-pCMV, candidates were selected in a streptomycin medium (Heermann R. et al., Simple generation of site-directed point mutations in the *Escherichia coli* chromosome using Red®/ET® Recombination. Microb. Cell Fact. 7, 14, 2008). DNA was isolated from the selected candidates using a DNA preparation method (Horsburgh B. C. et al., Genetic manipulation of herpes simplex virus using bacterial artificial chromosomes, Methods Enzymol. 1999. 306:337-352). The introduction of tkpA-EmGFP-pCMV at UL26/27 was confirmed through restriction enzyme EcoRI and XhoI treatment and PCR (polymerase chain reaction), and the exact gene sequence was identified through sequencing of the PCR product.

An experiment was conducted for normal expression of a fluorescent protein and production of a virus. The completed KOS-37/BAC-EmGFP-gD-R222N/F223I DNA was extracted using a large-construct DNA purification kit (Macherey-Nagel), after which $2\times10^5$ Cre-Vero-HVEM cells were transfected with 1 μg of DNA using a Lipofectamine 2000 reagent (Invitrogen) to remove the BAC gene using Cre recombinase. 3 days after transfection, expression of the EmGFP protein was observed using a fluorescence microscope, and viral production was observed through the formation of Cre-Vero-HVEM cell plaques. After confirmation of plaque formation, the virus-containing cells were collected, subjected three times to a freeze-thaw process (Gierasch W. W. et al., Construction and characterization of bacterial artificial chromosomes containing HSV-1 strains 17 and KOS, J. Virol. Methods. 2006. 135:197-206), and sonicated, thus obtaining a KOS-EmGFP-gD-R222N/F223I virus (gDm).

For infection with the KOS-EmGFP-gD-R222N/F223I virus and fluorescence expression thereof, HVEM-free cell lines (J1 and J-Nectin) and cell lines expressing HVEM (J-HVEM) were used. J1 cells are young hamster kidney cell lines that are deficient in the virus HSV-1 receptors HVEM and nectin-1 (Petrovic B. et al., Insertion of a ligand to HER2 in gB retargets HSV tropism and obviates the need for activation of the other entry glycoproteins. 2017. PLOS Pathog. 13 (4): e1006352). J-Nectin and J-HVEM cell lines are cell lines that overexpress nectin-1 and HVEM respectively in J1 cells (Petrovic B. et al., Insertion of a ligand to HER2 in gB retargets HSV tropism and obviates the need for activation of the other entry glycoproteins. 2017. PLOS Pathog. 13 (4): e1006352). Each cell line was cultured in DMEM (Welgene) containing 100 U/ml penicillin/100 μg/ml streptomycin (Welgene) and 10% FBS (fetal bovine serum, Welgene). $1\times10^4$ cells were infected at 10 MOI (multiplicity of infection) with the KOS-EmGFP-gD-R222N/F223I virus obtained above, and after 24 hours, the fluorescent protein expression and viral infection were observed using a fluorescence microscope (Baek H. J. et al., Bispecific Adapter-Mediated Retargeting of a Receptor-Restricted HSV-1 Vector to CEA-Bearing Tumor Cells, Mol. Ther. 2011. 19 (3): 507-514).

Figure 4:
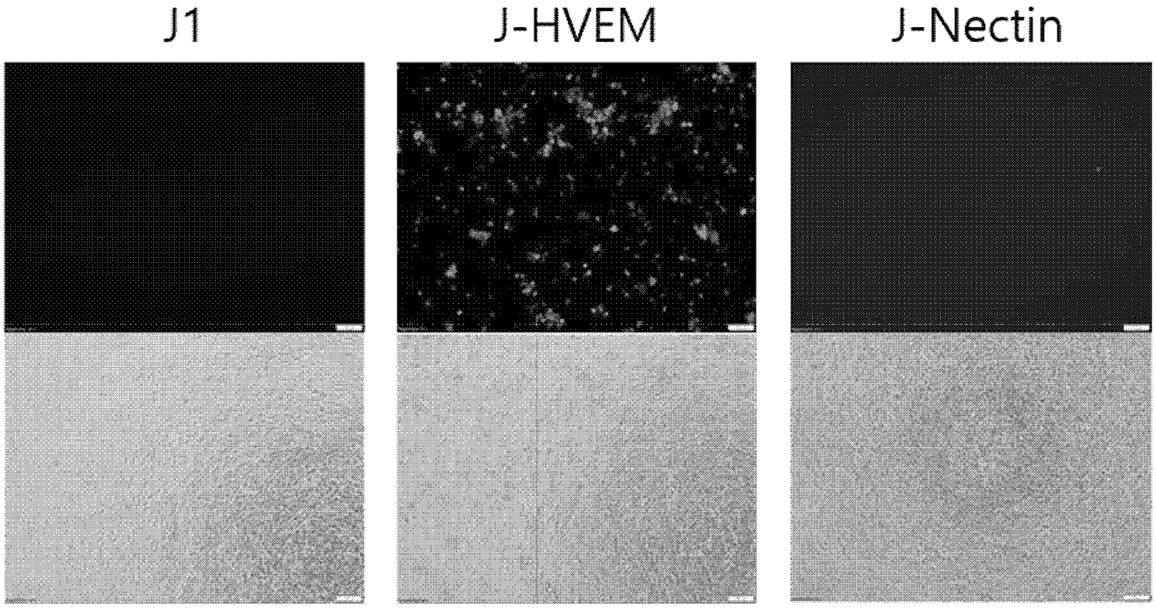
FIG. 4 shows the results of fluorescence expression of an HVEM-restricted HSV-1 virus expressing EmGFP and specific infection of cells having an HVEM receptor therewith.

The results thereof are shown in FIG. 4, upper and lower images of which were taken using a fluorescence microscope and an optical microscope, respectively. With reference to the upper fluorescence microscope images of FIG. 4, it can be seen that the JI cell line and the J-Nectin cell line were not infected, and only the J-HVEM cell line was infected.

Based on the above results, it was confirmed that the propagation of the KOS-EmGFP-gD-R222N/F223I virus (gDm) was easily observed through the expression of the fluorescent protein, as intended, and cell entry became possible using only HVEM as the entry receptor, without nectin-1.

<Example 3> Production of HSV-1 Having Modified Glycoprotein gH for Targeting HER2, HSV-1 Having Modified Glycoprotein gH for Targeting EpCAM, and HSV-1 Having Modified Glycoprotein gH for Targeting CEA For the production of a retargeting HSV capable of targeting a target molecule expressed in specific cancer, a ligand (scFv) that recognizes HER2, EpCAM or CEA specifically expressed in cancer cells was inserted between amino acids 29 and 30 of the amino acid sequence of gH (GenBank Accession No. ASM47773, SEQ ID NO: 1), which is a glycoprotein of HSV-1. A gene capable of expressing HER2scFv, EpCAMscFv, or CEAscFv was inserted between amino acids 29 and 30 of the glycoprotein gH in the KOS-37/BAC-EmGFP-gD-R222N/F223I DNA into which the EmGFP-expressing cassette (pCMV-EmGFP-tkpA) was inserted, manufactured in Example 2.

Figure 5:
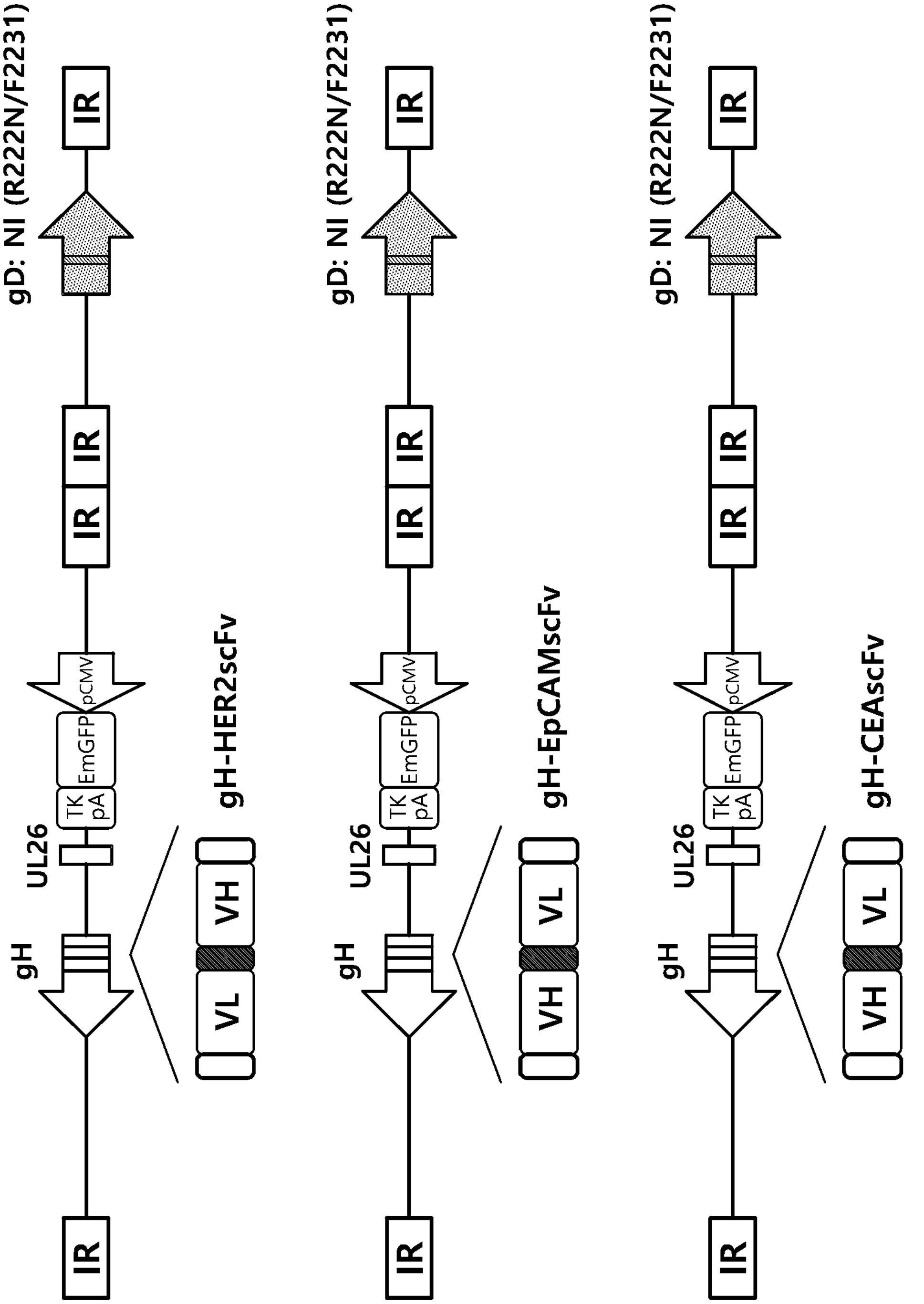
FIG. 5 schematically shows the genomic structure of each of HSV-1 having a modified glycoprotein gH for targeting HER2, HSV-1 having a modified glycoprotein gH for targeting EpCAM, and HSV-1 having a modified glycoprotein gH for targeting CEA.
Figure 6:
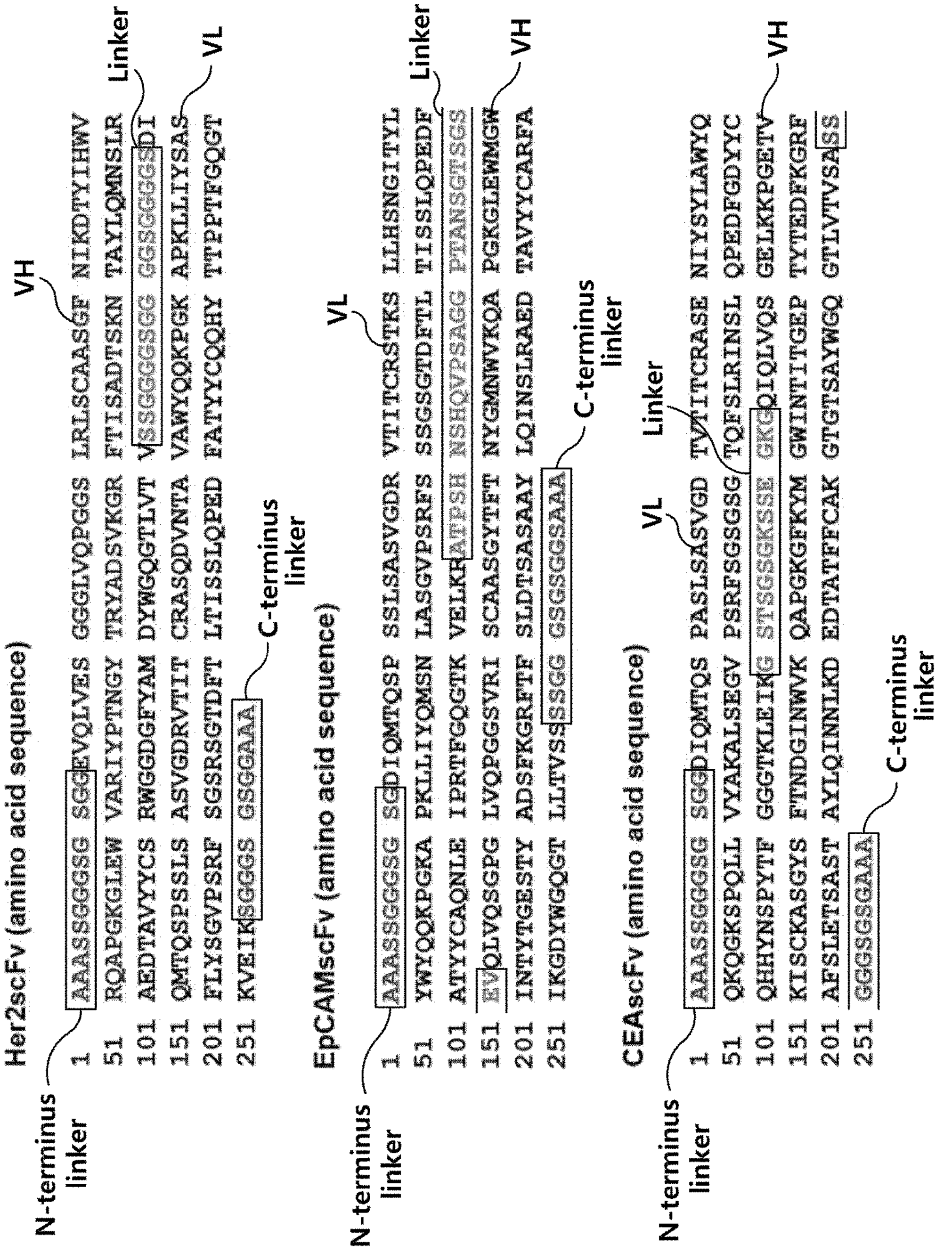
FIG. 6 shows the entire amino acid sequences of the HER2scFv (SEQ ID NO: 27) (wherein the N-terminus linker is SEQ ID NO: 19, the VH is SEQ ID NO: 4, the linker is SEQ ID NO: 24, the VL is SEQ ID NO: 5, and the C-terminus linker is SEQ ID NO: 20), gH-EpCAM2scFv (SEQ ID NO: 29) (wherein the N-terminus linker is SEQ ID NO: 22, the VL is SEQ ID NO: 6, the linker is SEQ ID NO: 21, the VH is SEQ ID NO: 7, and the C-terminus linker is SEQ ID NO: 23), and gH-CEAscFv (SEQ ID NO: 31) (wherein the N-terminus linker is SEQ ID NO: 25, the VL is SEQ ID NO: 8, the VH is SEQ ID NO: 9, and the C-terminus linker is SEQ ID NO: 26) ligands inserted into the gH glycoprotein and the configuration of the corresponding sequence.

The genomic structures of the KOS-gH/HER2scFv-EmGFP-gD/R222N/F223I virus, the KOS-gH/EpCAM-scFv-EmGFP-gD/R222N/F223I virus, and the KOS-gH/CEAscFv-EmGFP-gD/R222N/F223I virus, in which a HER2scFv ligand, an EpCAMscFv ligand, and a CEAscFv ligand, respectively, was inserted into gH of HSV-1, are schematically shown in FIG. 5, and the entire sequence of the HER2scFv ligand, the gH-EpCAM2scFv ligand or the gH-CEAscFv ligand inserted into the gH glycoprotein and the configuration of the corresponding sequence are shown in FIG. 6.

Here, scFv for HER2 is configured such that VH of SEQ ID NO: 4 and VL of SEQ ID NO: 5 are linked via a linker peptide of SEQ ID NO: 18, and the linker peptide of SEQ ID NO: 19 and the linker peptide of SEQ ID NO: 20 are linked to the N-terminus and the C-terminus of the HER2 scFv, respectively. Also, scFv for EpCAM is configured such that VL of SEQ ID NO: 6 and VH of SEQ ID NO: 7 are linked via a linker peptide of SEQ ID NO: 21, and the linker peptide of SEQ ID NO: 22 and the linker peptide of SEQ ID NO: 23 are linked to the N-terminus and the C-terminus of the EpCAM scFv, respectively. Also, scFv for CEA is configured such that VL of SEQ ID NO: 8 and VH of SEQ ID NO: 9 are linked via a linker peptide of SEQ ID NO: 24, and the linker peptide of SEQ ID NO: 25 and the linker peptide of SEQ ID NO: 26 are linked to the N-terminus and the C-terminus of the CEA scFv, respectively.

Used in the present example, the amino acid sequence and the gene sequence of the full length of the HER2scFv are represented in SEQ ID NO: 27 and SEQ ID NO: 28, respectively, the amino acid sequence and the gene sequence of the full length of the EpCAMscFv are represented in SEQ ID NO: 29 and SEQ ID NO: 30, respectively, and the amino acid sequence and the gene sequence of the full length of the CEAscFv are represented in SEQ ID NO: 31 and SEQ ID NO: 32, respectively.

The insertion of the HER2scFv ligand, the EpCAMscFv ligand or the CEAscFv ligand into gH was performed according to the manufacturer's protocol using a counter-selection BAC modification kit (GeneBridges Inc.), as in Examples 1 and 2.

Specifically, the *E. coli* clone containing the KOS-37/BAC-EmGFP-gD-R222N/F223I DNA manufactured in Example 2 was transformed with a pRed/ET plasmid expressing RecE and RecT capable of performing the function of homologous recombination (Muyrers J. P. et al., Rapid modification of bacterial artificial chromosomes by ET-recombination, Nucleic Acids Res. 1999. 27 (6): 1555-1557). A gH29/30-rpsL-neo/kan cassette was manufactured using a set of homologous region primers (forward primer gH29/30-rpsL-neo_for: SEQ ID NO: 33, reverse primer gH29/30-rpsL-neo_rev: SEQ ID NO: 34) including a locus at which to introduce a target gene between amino acids 29 and 30 of gH. The clone containing KOS37-EmGFP-gD-R222N/F223I DNA and pRed/ET was added with L-arabinose (Sigma-Aldrich) to thus induce homologous recombination, followed by transformation with 200 ng of the gH29/30-rpsL-neo/kan cassette manufactured as described above. Through such homologous recombination, the gH29/30-rpsL-neo/kan cassette is inserted at the position between amino acids 29 and 30 of gH of KOS-37/BAC-EmGFP-gD-R222N/F223I DNA. *E. coli* into which gH29/30-rpsL-neo/kan is inserted exhibits kanamycin resistance, but streptomycin resistance is blocked by the rpsL gene. It was inferred for *E. coli* obtained from the kanamycin medium that gH29/30-rpsL-neo/kan was inserted therein, and the final step of inserting a target gene was performed.

*E. coli* containing the gH29/30-rpsL-neo/kan cassette was added with L-arabinose (Sigma-Aldrich) activating the function of pRed/ET to thus induce homologous recombination, followed by transformation with 200 ng of each of a gH29/30-HER2scFv ligand, a gH29/30-EpCAMscFv ligand and a gH29/30-CEAscFv ligand. The gH29/30-HER2scFv ligand, the gH29/30-EpCAMscFv ligand, and the gH29/30-CEAscFv ligand were manufactured using a forward primer gH29/30-scFv_For (SEQ ID NO: 35) and a reverse primer gH29/30-scFv_Rev (SEQ ID NO: 36) using, as respective templates, a pCAGGSMCS-gH-HER2scFv plasmid, a pCAGGSMCS-gH-EpCAMscFv plasmid, and a pCAGGSMCS-gH-CEAscFv plasmid. The pCAGGSMCS-gH-HER2scFv plasmid, the pCAGGSMCS-gH-EpCAM-scFv plasmid, and the pCAGGSMCS-gH-CEAscFv plasmid were manufactured by inserting respective scFv genes into MCS of a pCAGGSMCS plasmid (Atanasiu D. et al., Dual split protein-based fusion assay reveals that mutations to herpes simplex virus (HSV) glycoprotein gB alter the kinetics of cell-cell fusion induced by HSV entry glycoproteins. J. Virol. 2013 November 87 (21): 11332-11345).

Based on the principle whereby streptomycin resistance blocked by rpsL is activated upon replacing the conventionally inserted gH29/30-rpsL-neo/kan cassette with the above-inserted gH29/30-target scFv, candidates were selected in a streptomycin medium (Heermann R. et al., Simple generation of site-directed point mutations in the *Escherichia coli* chromosome using Red®/ET® Recombination. Microb. Cell Fact. 7, 14, 2008). DNA was isolated from the selected candidates using a DNA preparation method (Horsburgh B. C. et al., Genetic manipulation of herpes simplex virus using bacterial artificial chromosomes, Methods Enzymol. 1999. 306:337-352). The introduction of each scFv at gH29/30 was confirmed through restriction enzyme EcoRI and XhoI treatment and PCR (polymerase chain reaction), and the exact gene sequence was identified through sequencing of the PCR product.

The completed KOS-37/BAC-gH/HER2scFv-EmGFP-gD-R222N/F223I DNA, KOS-37/BAC-gH/EpCAMscFv-EmGFP-gD-R222N/F223I DNA, and KOS-37/BAC-gH/CEAscFv-EmGFP-gD-R222N/F223I DNA were extracted using a large-construct DNA purification kit (Macherey-Nagel), after which $2\times10^5$ Cre-Vero-HVEM cells were transfected with 1 μg of DNA using a Lipofectamine 2000 reagent (Invitrogen) to remove the BAC gene using Cre recombinase. 3 days after transfection, the fluorescence expression of the EmGFP protein and the formation of cell plaques were observed using a fluorescence microscope. After confirmation of plaque formation, the virus-containing cells were collected, subjected three times to a freeze-thaw process (Gierasch W. W. et al., Construction and characterization of bacterial artificial chromosomes containing HSV-1 strains 17 and KOS, J. Virol. Methods. 2006. 135: 197-206), and sonicated, ultimately obtaining a KOS-gH/HER2scFv-EmGFP-gD-R222N/F223I virus (gH-scHER2), a KOS-gH/EpCAMscFv-EmGFP-gD-R222N/F223I virus (gH-scEpCAM), and a KOS-gH/CEAscFv-EmGFP-gD-R222N/F223I virus (gH-scCEA).

<Example 4> Infection and Cytotoxicity of HER2-Expressing Cancer Cells Using HSV-1 Virus Having Modified Glycoprotein gH for Targeting HER2

In order to confirm whether the KOS-gH/HER2scFv-EmGFP-gD-R222N/F223I virus (gH-scHER2) manufactured in Example 3 induces viral infection into surrounding cancer cells using the HER2scFv ligand expressed in the glycoprotein gH and whether it induces cell death after infection, the following experiment was conducted.

The cell lines that were used in the experiment were a cell line not expressing HER2 (MDA-MB-231) and cell lines expressing HER2 (SK-OV-3, MCF7, and MDA-MB-231). For breast cancer cell lines MDA-MB-231 (ATCC, HTB-26) and MCF-7 (ATCC, HTB-22) and an ovarian cancer cell line SK-OV-3 (ATCC, HTB-77), culture was performed using DMEM containing 100 U/ml penicillin/100 μg/ml streptomycin (Welgene) and 10% FBS. For a breast cancer cell line MDA-MB-453 (ATCC, HTB-131), culture was performed using an RPMI 1640 medium (Welgene) containing 100 U/ml penicillin/100 μg/ml streptomycin (Welgene) and 10% FBS.

For HER2-specific viral infection, $1\times10^4$ SK-OV-3 and MDA-MB-231 cell lines were used at 2 MOI and infected with the virus (gH-scHER2) expressing the HER2scFv ligand in gH manufactured in Example 3 and the virus (gDm) not expressing the HER2scFv ligand as a control. After 90 minutes, the medium that was used was replaced with a fresh medium in order to remove the remaining initial virus. 2 days after infection, viral infection was confirmed through fluorescence expression in each cell line. In order to measure cell death for 5 days, the cytotoxicity of cancer cell lines due to each virus after treatment with an EZ-Cytox (DoGenBio) reagent was observed using a fluorescence microscope. Also, in order to measure cytotoxicity for 4 days after infection, the extent of color development of formazan, which is a color-developing material formed only in living cells using an EZ-Cytox (DoGenBio) reagent, was measured at 450 nm using an ELISA reader. Absorbance was quantified to determine the cytotoxicity of cancer cell lines due to each virus.

Figure 7:
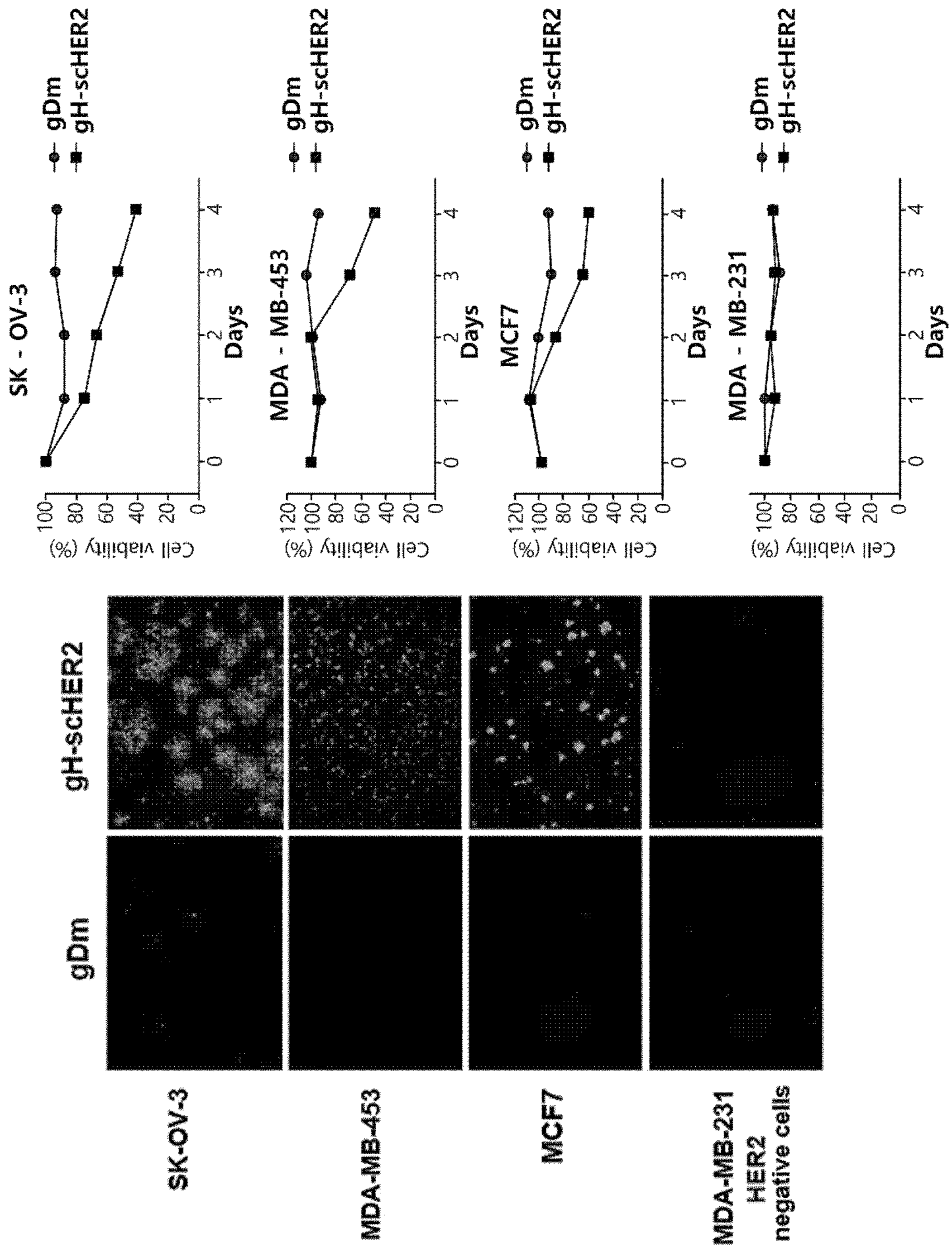
FIG. 7 shows the results of specific infection and cell death of a HER2-expressing cancer cell by the HSV-1 virus having a modified glycoprotein gH for targeting HER2.

The results thereof are shown in FIG. 7. As is apparent from FIG. 7, in MDA-MB-231 not expressing HER2, both the gH-scHER2 virus expressing the HER2scFv ligand in gH and the gDm virus not expressing the HER2scFv ligand were uninfected, so fluorescence was not observed. However, it can be confirmed that the HER2-expressing cell lines SK-OV-3, MDA-MB-453, and MCF-7 were specifically infected with the gH-scHER2 virus expressing the HER2scFv ligand, and thus fluorescence was observed.

In addition, FIG. 7 shows the results of observation of cytotoxicity of cancer cells due to the virus for 5 days after infection. In MDA-MB-231 not expressing HER2, cell death did not occur due to the gH-scHER2 virus expressing the HER2scFv ligand or due to the gDm virus not expressing the HER2scFv ligand. However, SK-OV-3, MDA-MB-453, and MCF-7, which are cell lines expressing HER2, were observed to have cell viability values of 41%, 61%, and 49%, respectively, due only to the gH-scHER2 virus expressing the HER2scFv ligand in gH. In conclusion, it was confirmed that the gH-scHER2 virus expressing the HER2scFv ligand in gH effectively induces specific infection and cytotoxicity of cancer cells expressing HER2.

<Example 5> Infection and Cytotoxicity of EpCAM-Expressing Cancer Cells Using HSV-1 Virus Having Modified Glycoprotein gH for Targeting EpCAM In order to confirm whether the KOS-gH/EpCAMscFv-EmGFP-gD-R222N/F2231 virus (gH-scEpCAM) manufactured in Example 3 induces viral infection into surrounding cancer cells due to the EpCAMscFv ligand expressed in the glycoprotein gH and whether it induces cell death after infection, the following experiment was conducted.

The cell lines that were used in the experiment were a cell line not expressing EpCAM (Mia-PaCa-2) and cell lines expressing EpCAM (MCF-7, MDA-MB-453, and BT-474). For breast cancer cell lines MCF-7 (ATCC, HTB-22) and BT-474 (ATCC, HTB-20) and a pancreatic cancer cell line Mia-PaCa-2 (ATCC, CRL-1420), culture was performed using DMEM containing 100 U/ml penicillin/100 μg/ml streptomycin (Welgene)) and 10% FBS, and for a breast cancer cell line MDA-MB-453 (ATCC, HTB-131), culture was performed using an RPMI medium containing 100 U/ml penicillin/100 μg/ml streptomycin (Welgene)) and 10% FBS.

For EpCAM-specific viral infection, $4.0\times10^4$ MCF-7, $8.0\times10^4$ MDA-MB-453, and $7.0\times10^4$ BT-474 cell lines were used at 2 MOI and infected with the virus (gH-scEpCAM) expressing the EpCAMscFv ligand in gH manufactured in Example 3 and the virus (gDm) not expressing the EpCAMscFv ligand as a control. After 90 minutes, the medium that was used was replaced with a fresh medium in order to remove the remaining initial virus. 2 days after infection, viral infection was confirmed through fluorescence expression in each cell line (Baek H. J. et al., Bispecific Adapter-Mediated Retargeting of a Receptor-Restricted HSV-1 Vector to CEA-Bearing Tumor Cells, Mol. Ther. 2011. 19 (3): 507-514). Also, in order to measure cytotoxicity for 5 days after infection, the extent of color development of formazan, which is a color-developing material formed only in living cells using an EZ-Cytox (DoGenBio) reagent, was measured at 450 nm using an ELISA reader. Absorbance was quantified to determine the cytotoxicity of cancer cell lines due to each virus.

Figure 8:
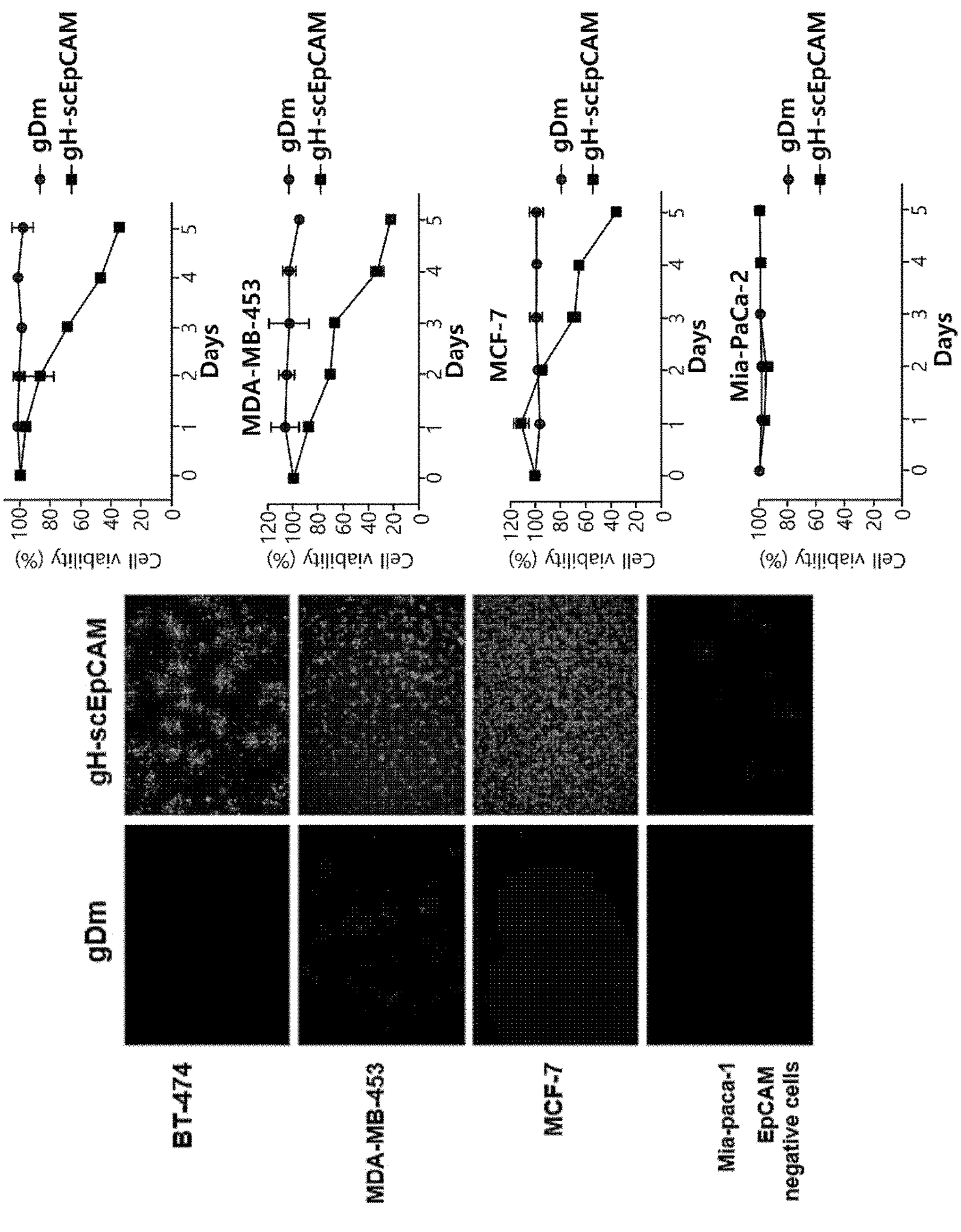
FIG. 8 shows the results of specific infection and cell death of an EpCAM-expressing cancer cell by the HSV-1 virus having a modified glycoprotein gH for targeting EpCAM.

The results thereof are shown in FIG. 8. As is apparent from FIG. 8, in Mia-PaCa-2 not expressing EpCAM, both the virus (gH-scEpCAM) expressing the EpCAMscFv ligand and the virus (gDm) not expressing the EpCAMscFv ligand, which is a control, were uninfected, so fluorescence was not observed. However, it can be confirmed that the EpCAM-expressing cell lines SK-OV-3, MDA-MB-453, and MCF-7 were specifically infected only with the virus (gH-scEpCAM) expressing the EpCAMscFv ligand, and thus fluorescence was observed.

In addition, FIG. 8 shows the results of observation of cytotoxicity of cancer cells due to the virus for 5 days after infection. In Mia-PaCa-2 not expressing EpCAM, cell death did not occur due to the virus (gH-scEpCAM) expressing the EpCAMscFv ligand or due to the virus (gDm) not expressing the EpCAMscFv ligand, which is a control. However, the cell lines expressing EpCAM, for example, BT-474, MDA-MB-453, and MCF-7, were observed to have cell viability values of 35%, 22% and 36%, respectively, due only to the virus (gH-scEpCAM) expressing the EpCAMscFv ligand. In conclusion, it was confirmed that the virus expressing the EpCAMscFv ligand in gH effectively induces specific infection and cell death of cancer cells expressing EpCAM.

<Example 6> Infection and Cytotoxicity of CEA-Expressing Cancer Cells Using HSV-1 Virus Having Modified Glycoprotein gH for Targeting CEA In order to confirm whether the KOS-gH/CEAscFv-EmGFP-gD-R222N/F2231 virus (gH-scCEA) manufactured in Example 3 induces viral infection into surrounding cancer cells due to the CEAscFv ligand expressed in the glycoprotein gH, the following experiment was conducted.

The cell lines that were used in the experiment were a cell line (CHO-K1) not expressing CEA and a cell line (CHO-CEA) expressing CEA. The Chinese hamster ovary cell lines CHO-K1 and CHO-CEA (Kuroki M. et al., J Biol. Chem. 1991. 74:10132-10141) were cultured using a HaM's F-12K medium (Welgene) containing 100 U/ml penicillin/100 μg/ml streptomycin (Welgene) and 10% FBS (fetal bovine serum).

For EpCAM-specific viral infection, $2.5\times10^4$ CHO-K1 and CHO-CEA cell lines were used at 20 MOI and infected with the virus (gH-scCEA) expressing the CEAscFv ligand in gH manufactured in Example 3 and the virus (gDm) not expressing the EpCAMscFv ligand as a control. After 90 minutes, the medium that was used was replaced with a fresh medium in order to remove the remaining initial virus. 2 days after infection, viral infection was confirmed through fluorescence expression in each cell line (Baek H. J. et al., Bispecific Adapter-Mediated Retargeting of a Receptor-Restricted HSV-1 Vector to CEA-Bearing Tumor Cells, Mol. Ther. 2011. 19 (3): 507-514).

Figure 9:
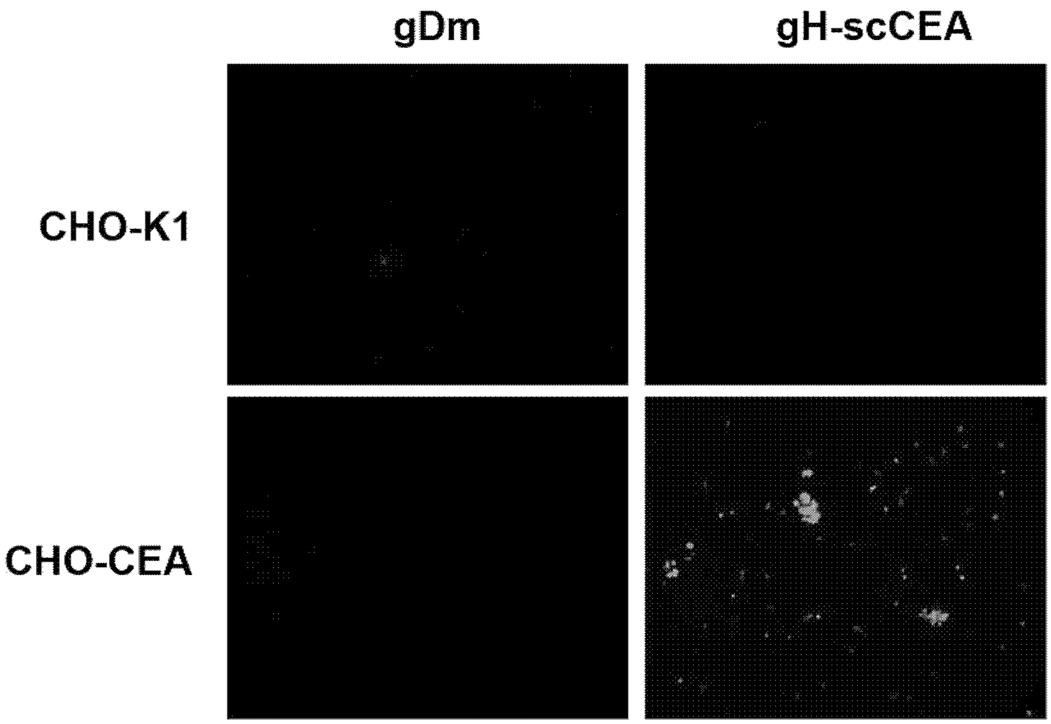
FIG. 9 shows the results of specific infection of a CEA-expressing cancer cell by the HSV-1 virus having a modified glycoprotein gH for targeting CEA.

The results thereof are shown in FIG. 9. As is apparent from FIG. 9, in CHO-K1 not expressing CEA, both the virus (gH-scCEA) expressing the CEAscFv ligand in gH and the virus (gDm) not expressing the EpCAMscFv ligand as a control were uninfected, so fluorescence was not observed. However, in CHO-CEA, which is a cell line expressing CEA, it can be confirmed that fluorescence was observed due to specific infection only with the virus (gH-scCEA) expressing the CEAscFv ligand. In conclusion, it was confirmed that the virus expressing the CEAscFv ligand in gH effectively induces specific infection of CEA-expressing cells.

What is claimed is:

1. A recombinant herpes simplex virus, configured such that a cell-targeting domain, which specifically recognizes and binds to a target molecule of a target cell, is inserted and fused into a glycoprotein gH, wherein the cell-targeting domain is inserted and fused into a position between the region of amino acids 29 and 30 in the amino acid sequence of the gH glycoprotein comprising SEQ ID NO: 1.

2. The recombinant herpes simplex virus of claim 1, wherein the recombinant herpes simplex virus is configured such that an additional cell-targeting domain is inserted into gB, gC or gD.

3. The recombinant herpes simplex virus of claim 1, wherein, when the cell-targeting domain is inserted and fused, a linker peptide is present at the N-terminus and the C-terminus of the cell-targeting domain, and the linker peptide comprises at least one amino acid selected from the group consisting of Ser, Gly, Ala, and Thr.

4. The recombinant herpes simplex virus of claim 1, wherein the target cell is a diseased cell, and the target molecule is an antigen or a receptor present on the surface of the diseased cell.

5. The recombinant herpes simplex virus of claim 1, wherein the target cell is a cancer cell, and the target molecule is an antigen or a receptor present on the surface of the cancer cell.

6. The recombinant herpes simplex virus of claim 5, wherein the antigen or the receptor is EGFRvIII (epidermal growth factor receptor variant III), EGFR (epidermal growth factor receptor), a metastin receptor, a receptor tyrosine kinase, HER2 (human epidermal growth factor receptor 2), a tyrosine kinase-18-receptor (c-Kit), HGF (hepatocyte growth factor) receptor c-Met, CXCR4 (C-X-C chemokine receptor type 4), CCR7 (C-C chemokine receptor type 7), an endothelin-A receptor, PPAR-δ (peroxisome proliferator activated receptor ϵ), PDGFR-α (platelet-derived growth factor receptor α), CD133 (cluster of differentiation 133), CEA (carcinoembryonic antigen), EpCAM (epithelial cell adhesion molecule), MSLN (mesothelin), GD2 (disialoganglioside), GPC3 (Glypican 3), PSMA (prostate-specific membrane antigen), TAG-72 (tumor-associated glycoprotein 72), GD3 (disialoganglioside), HLA-DR (human leukocyte antigen-DR), MUC1 (Mucin 1), NY-ESO-1 (New York esophageal squamous cell carcinoma 1), LMP1 (latent membrane protein 1), TRAILR2 (tumor-necrosis factor-related apoptosis-inducing ligand receptor), VEGFR2 (vascular endothelial growth factor receptor 2), HGFR (hepatocyte growth factor receptor), CD44, or CD166.

7. The recombinant herpes simplex virus of claim 1, wherein the target molecule is HER2, and the targeting domain is a single-chain variable fragment (scFv) for HER2, configured such that the heavy chain variable domain (VH) of SEQ ID NO: 4 and the light chain variable domain (VL) of SEQ ID NO: 5 are linked in an order of VH, a linker peptide, and VL via the linker peptide.

8. The recombinant herpes simplex virus of claim 1, wherein the target molecule is EpCAM, and the targeting domain is an scFv for EpCAM, configured such that the VL of SEQ ID NO: 6 and the VH of SEQ ID NO: 7 are linked in an order of VL, a linker peptide, and VH via the linker peptide.

9. The recombinant herpes simplex virus of claim 1, wherein the target molecule is CEA, and the targeting domain is an scFv for CEA, configured such that the VL of SEQ ID NO: 8 and the VH of SEQ ID NO: 9 are linked in an order of VL, a linker peptide, and VH via the linker peptide.

10. The recombinant herpes simplex virus of claim 7, wherein a linker peptide of SEQ ID NO: 19 is linked to the N-terminus of the scFv, and a linker peptide of SEQ ID NO: 20 is linked to the C-terminus of the scFv.

11. The recombinant herpes simplex virus of claim 8, wherein a linker peptide of SEQ ID NO: 22 is linked to the N-terminus of the scFv, and a linker peptide of SEQ ID NO: 23 is linked to the C-terminus of the scFv.

12. The recombinant herpes simplex virus of claim 9, wherein a linker peptide of SEQ ID NO: 25 is linked to the N-terminus of the scFv, and a linker peptide of SEQ ID NO: 26 is linked to the C-terminus of the scFv.

13. The recombinant herpes simplex virus of claim 1, wherein the recombinant herpes simplex virus is configured such that the arginine (R) at position 222 and the phenylalanine (F) at position 223 of an amino acid sequence of gD (glycoprotein D) of SEQ ID NO: 10 are substituted with asparagine (N) and isoleucine (I), respectively.

14. The recombinant herpes simplex virus of claim 1, wherein the recombinant herpes simplex virus is a recombinant HSV-1 virus, a recombinant HSV-2 virus, or an HSV-1 and HSV-2 chimeric virus.

15. The recombinant herpes simplex virus of claim 1, wherein the recombinant herpes simplex virus is a recombinant HSV-1 derived from an HSV-1 Kendall Owen Smith (KOS) strain.

16. The recombinant herpes simplex virus of claim 1, wherein the recombinant herpes simplex virus is configured such that an expression cassette expressing at least one selected from the group consisting of (i) a cytokine, (ii) a chemokine, (iii) an antagonist to an immune checkpoint, (iv) a co-stimulatory factor, which induces activation of an immune cell, (v) an antagonist to TGFβ (transforming growth factor β), which inhibits an immune response to a cancer cell, (vi) heparanase, which degrades heparan sulfate proteoglycan for a solid tumor microenvironment, (vii) an antagonist, which inhibits a function of an angiogenesis factor receptor VEGFR-2 (VEGF receptor-2), and (viii) a prodrug-activating enzyme, which converts a prodrug into a drug that exhibits toxicity to a cancer cell, is inserted into the genome of the herpes simplex virus without inhibiting propagation of the herpes simplex virus.

17. The recombinant herpes simplex virus of claim 16, wherein the cytokine is at least one interleukin selected from the group consisting of IL-2, IL-4, IL-7, IL-10, IL-12, IL-15, IL-18 and IL-24, at least one interferon selected from the group consisting of IFNα, IFNβ and IFNγ, or at least one tumor necrosis factor selected from the group consisting of TNFα, granulocyte-macrophage colony-stimulating factor (GM-CSF), granulocyte-colony stimulating factor (G-CSF), and FMS-like tyrosine kinase 3 ligand (FLT3L), the chemokine is at least one selected from among the group consisting of CCL2 (C-C motif chemokine ligand 2), Regulated upon Activation, normal T cell Expressed and Secreted (RANTES), CCL7, CCL9, CCL10, CCL12, CCL15, CCL19, CCL21, CCL20, and X-C motif chemokine ligand (XCL-1), the immune checkpoint antagonist is at least one selected from the group consisting of PD-1 (programmed cell death 1), PD-L1 (programmed cell death ligand 1), PD-L2 (programmed cell death ligand 2), CD27 (cluster of differentiation 27), CD28 (cluster of differentiation 28), CD70 (cluster of differentiation 70), CD80 (cluster of differentiation 80), CD86 (cluster of differentiation 86), CD137 (cluster of differentiation 137), CD276 (cluster of differentiation 276), KIR (killer-cell immunoglobulin-like receptor), LAG3 (lymphocyte activation gene 3), GITR (glucocorticoid-induced TNFR-related protein), GITRL (glucocorticoid-induced TNFR-related protein ligand), and CTLA-4 (cytolytic T lymphocyte associated antigen-4), the co-stimulatory factor is at least one selected from the group consisting of CD2, CD7, homologous to lymphotoxin, exhibits inducible expression and competes with HSV glycoprotein D for herpesvirus entry mediator, a receptor expressed on T cells (LIGHT), NKG2-C type II integral membrane protein (NKG2C), CD27, CD28, 4-1BB, OX40, CD30, CD40, LFA-1 (lymphocyte function-associated antigen-1), ICOS (inducible T cell co-stimulator), CD3γ, CD3ϵ, and CD3ε, and the prodrug-activating enzyme is at least one selected from the group consisting of cytosine deaminase, rat cytochrome P450 (CYP2B1), carboxylesterase, bacterial nitroreductase, and PNP (purine nucleoside phosphorylase) isolated from *E. coli*.

18. A pharmaceutical composition for treating cancer, comprising the recombinant herpes simplex virus of claim 1 as an active ingredient.

* * * * *

```
                         SEQUENCE LISTING

<160> NUMBER OF SEQ ID NOS: 36

<210> SEQ ID NO 1
<211> LENGTH: 838
<212> TYPE: PRT
<213> ORGANISM: Artificial Sequence
<220> FEATURE:
<223> OTHER INFORMATION: gH

<400> SEQUENCE: 1

Met Gly Asn Gly Leu Trp Phe Val Gly Val Ile Leu Leu Gly Val Ala
1               5                   10                  15

Trp Gly Gln Val His Asp Trp Thr Glu Gln Thr Asp Pro Trp Phe Leu
            20                  25                  30

Asp Gly Leu Gly Met Asp Arg Met Tyr Trp Arg Asp Thr Asn Thr Gly
        35                  40                  45

Arg Leu Trp Leu Pro Asn Thr Pro Asp Pro Gln Lys Pro Pro Arg Gly
    50                  55                  60

Phe Leu Ala Pro Pro Asp Glu Leu Asn Leu Thr Thr Ala Ser Leu Pro
65                  70                  75                  80

Leu Leu Arg Trp Tyr Glu Glu Arg Phe Cys Phe Val Leu Val Thr Thr
                85                  90                  95

Ala Glu Phe Pro Arg Asp Pro Gly Gln Leu Leu Tyr Ile Ser Lys Thr
            100                 105                 110

Tyr Leu Leu Gly Arg Pro Pro Asn Ala Ser Leu Pro Ala Pro Ile Thr
        115                 120                 125

Val Glu Pro Thr Ala Gln Pro Pro Pro Ala Val Ala Pro Leu Lys Gly
    130                 135                 140

Leu Leu His Asn Pro Thr Ala Ser Val Leu Leu Arg Ser Arg Ala Trp
145                 150                 155                 160

Val Thr Phe Ser Ala Val Pro Asp Pro Glu Ala Leu Thr Phe Pro Arg
                165                 170                 175

Gly Asp Asn Val Ala Thr Ala Ser His Pro Ser Gly Pro Arg Asp Thr
            180                 185                 190

Pro Pro Pro Arg Pro Pro Val Gly Ala Arg Arg His Pro Thr Thr Glu
        195                 200                 205

Leu Asp Ile Thr His Leu His Asn Ala Ser Thr Thr Trp Leu Ala Thr
    210                 215                 220

Arg Gly Leu Leu Arg Ser Pro Gly Arg Tyr Val Tyr Phe Ser Pro Ser
225                 230                 235                 240

Ala Ser Thr Trp Pro Val Gly Ile Trp Thr Thr Gly Glu Leu Val Leu
                245                 250                 255

Gly Cys Asp Ala Ala Leu Val Arg Ala Arg Tyr Gly Arg Glu Phe Met
            260                 265                 270

Gly Leu Val Ile Ser Met His Asp Ser Pro Pro Val Glu Val Met Val
```

-continued

```
        275                 280                 285

Val Pro Ala Gly Gln Thr Leu Asp Arg Val Gly Asp Pro Ala Asp Glu
    290                 295                 300

Asn Pro Pro Gly Ala Leu Pro Gly Pro Pro Gly Gly Pro Arg Tyr Arg
305                 310                 315                 320

Val Phe Val Leu Gly Ser Leu Thr Arg Ala Asp Asn Gly Ser Ala Leu
                325                 330                 335

Asp Ala Leu Arg Arg Val Gly Gly Tyr Pro Glu Glu Gly Thr Asn Tyr
            340                 345                 350

Ala Gln Phe Leu Ser Arg Ala Tyr Ala Glu Phe Phe Ser Gly Asp Ala
        355                 360                 365

Gly Ala Glu Gln Gly Pro Arg Pro Pro Leu Phe Trp Arg Leu Thr Gly
    370                 375                 380

Leu Leu Ala Thr Ser Gly Phe Ala Phe Val Asn Ala Ala His Ala Asn
385                 390                 395                 400

Gly Ala Val Cys Leu Ser Asp Leu Leu Gly Phe Leu Ala His Ser Arg
                405                 410                 415

Ala Leu Ala Gly Leu Ala Ala Arg Gly Ala Ala Gly Cys Ala Ala Asp
            420                 425                 430

Ser Val Phe Phe Asn Val Ser Val Leu Asp Pro Thr Ala Arg Leu Gln
        435                 440                 445

Leu Glu Ala Arg Leu Gln His Leu Val Ala Glu Ile Leu Glu Arg Glu
    450                 455                 460

Gln Ser Leu Ala Leu His Ala Leu Gly Tyr Gln Leu Ala Phe Val Leu
465                 470                 475                 480

Asp Ser Pro Ser Ala Tyr Asp Ala Val Ala Pro Ser Ala Ala His Leu
                485                 490                 495

Ile Asp Ala Leu Tyr Ala Glu Phe Leu Gly Gly Arg Val Leu Thr Thr
            500                 505                 510

Pro Val Val His Arg Ala Leu Phe Tyr Ala Ser Ala Val Leu Arg Gln
        515                 520                 525

Pro Phe Leu Ala Gly Val Pro Ser Ala Val Gln Arg Glu Arg Ala Arg
    530                 535                 540

Arg Ser Leu Leu Ile Ala Ser Ala Leu Cys Thr Ser Asp Val Ala Ala
545                 550                 555                 560

Ala Thr Asn Ala Asp Leu Arg Thr Ala Leu Ala Arg Ala Asp His Gln
                565                 570                 575

Lys Thr Leu Phe Trp Leu Pro Asp His Phe Ser Pro Cys Ala Ala Ser
            580                 585                 590

Leu Arg Phe Asp Leu Asp Glu Ser Val Phe Ile Leu Asp Ala Leu Ala
        595                 600                 605

Gln Ala Thr Arg Ser Glu Thr Pro Val Glu Val Leu Ala Gln Gln Thr
    610                 615                 620

His Gly Leu Ala Ser Thr Leu Thr Arg Trp Ala His Tyr Asn Ala Leu
625                 630                 635                 640

Ile Arg Ala Phe Val Pro Glu Ala Ser His Arg Cys Gly Gly Gln Ser
                645                 650                 655

Ala Asn Val Glu Pro Arg Ile Leu Val Pro Ile Thr His Asn Ala Ser
            660                 665                 670

Tyr Val Val Thr His Ser Pro Leu Pro Arg Gly Ile Gly Tyr Lys Leu
        675                 680                 685

Thr Gly Val Asp Val Arg Arg Pro Leu Phe Leu Thr Tyr Leu Thr Ala
    690                 695                 700
```

```
Thr Cys Glu Gly Ser Thr Arg Asp Ile Glu Ser Lys Arg Leu Val Arg
705                 710                 715                 720

Thr Gln Asn Gln Arg Asp Leu Gly Leu Val Gly Ala Val Phe Met Arg
                725                 730                 735

Tyr Thr Pro Ala Gly Glu Val Met Ser Val Leu Leu Val Asp Thr Asp
            740                 745                 750

Asn Thr Gln Gln Gln Ile Ala Ala Gly Pro Thr Glu Gly Ala Pro Ser
        755                 760                 765

Val Phe Ser Ser Asp Val Pro Ser Thr Ala Leu Leu Leu Phe Pro Asn
    770                 775                 780

Gly Thr Val Ile His Leu Leu Ala Phe Asp Thr Gln Pro Val Ala Ala
785                 790                 795                 800

Ile Ala Pro Gly Phe Leu Ala Ala Ser Ala Leu Gly Val Val Met Ile
                805                 810                 815

Thr Ala Ala Leu Ala Gly Ile Leu Lys Val Leu Arg Thr Ser Val Pro
            820                 825                 830

Phe Phe Trp Arg Arg Glu
        835


<210> SEQ ID NO 2
<211> LENGTH: 904
<212> TYPE: PRT
<213> ORGANISM: Artificial Sequence
<220> FEATURE:
<223> OTHER INFORMATION: gB

<400> SEQUENCE: 2

Met His Gln Gly Ala Pro Ser Trp Gly Arg Arg Trp Phe Val Val Trp
1               5                   10                  15

Ala Leu Leu Gly Leu Thr Leu Gly Val Leu Val Ala Ser Ala Ala Pro
            20                  25                  30

Ser Ser Pro Gly Thr Pro Gly Val Ala Ala Ala Thr Gln Ala Ala Asn
        35                  40                  45

Gly Gly Pro Ala Thr Pro Ala Pro Pro Ala Leu Gly Ala Ala Pro Thr
    50                  55                  60

Gly Asp Pro Lys Pro Lys Lys Asn Lys Lys Pro Lys Asn Pro Thr Pro
65                  70                  75                  80

Pro Arg Pro Ala Gly Asp Asn Ala Thr Val Ala Ala Gly His Ala Thr
                85                  90                  95

Leu Arg Glu His Leu Arg Asp Ile Lys Ala Glu Asn Thr Asp Ala Asn
            100                 105                 110

Phe Tyr Val Cys Pro Pro Pro Thr Gly Ala Thr Val Val Gln Phe Glu
        115                 120                 125

Gln Pro Arg Arg Cys Pro Thr Arg Pro Glu Gly Gln Asn Tyr Thr Glu
    130                 135                 140

Gly Ile Ala Val Val Phe Lys Glu Asn Ile Ala Pro Tyr Lys Phe Lys
145                 150                 155                 160

Ala Thr Met Tyr Tyr Lys Asp Val Thr Val Ser Gln Val Trp Phe Gly
                165                 170                 175

His Arg Tyr Ser Gln Phe Met Gly Ile Phe Glu Asp Arg Ala Pro Val
            180                 185                 190

Pro Phe Glu Glu Val Ile Asp Lys Ile Asn Ala Lys Gly Val Cys Arg
        195                 200                 205

Ser Thr Ala Lys Tyr Val Arg Asn Asn Leu Glu Thr Thr Ala Phe His
    210                 215                 220
```

-continued

```
Arg Asp Asp His Glu Thr Asp Met Glu Leu Lys Pro Ala Asn Ala Ala
225                 230                 235                 240

Thr Arg Thr Ser Arg Gly Trp His Thr Thr Asp Leu Lys Tyr Asn Pro
                245                 250                 255

Ser Arg Val Glu Ala Phe His Arg Tyr Gly Thr Thr Val Asn Cys Ile
            260                 265                 270

Val Glu Glu Val Asp Ala Arg Ser Val Tyr Pro Tyr Asp Glu Phe Val
        275                 280                 285

Leu Ala Thr Gly Asp Phe Val Tyr Met Ser Pro Phe Tyr Gly Tyr Arg
    290                 295                 300

Glu Gly Ser His Thr Glu His Thr Ser Tyr Thr Ala Asp Arg Phe Lys
305                 310                 315                 320

Gln Val Asp Gly Phe Tyr Ala Arg Asp Leu Thr Thr Lys Ala Arg Ala
                325                 330                 335

Thr Ala Pro Thr Thr Arg Asn Leu Leu Thr Thr Pro Lys Phe Thr Val
            340                 345                 350

Ala Trp Asp Trp Val Pro Lys Arg Pro Ser Val Cys Thr Met Thr Lys
        355                 360                 365

Trp Gln Glu Val Asp Glu Met Leu Arg Ser Glu Tyr Gly Gly Ser Phe
    370                 375                 380

Arg Phe Ser Ser Asp Ala Ile Ser Thr Thr Phe Thr Thr Asn Leu Thr
385                 390                 395                 400

Glu Tyr Pro Leu Ser Arg Val Asp Leu Gly Asp Cys Ile Gly Lys Asp
                405                 410                 415

Ala Arg Asp Ala Met Asp Arg Ile Phe Ala Arg Arg Tyr Asn Ala Thr
            420                 425                 430

His Ile Lys Val Gly Gln Pro Gln Tyr Tyr Leu Ala Asn Gly Gly Phe
        435                 440                 445

Leu Ile Ala Tyr Gln Pro Leu Leu Ser Asn Thr Leu Ala Glu Leu Tyr
    450                 455                 460

Val Arg Glu His Leu Arg Glu Gln Ser Arg Lys Pro Pro Asn Pro Thr
465                 470                 475                 480

Pro Pro Pro Pro Gly Ala Ser Ala Asn Ala Ser Val Glu Arg Ile Lys
                485                 490                 495

Thr Thr Ser Ser Ile Glu Phe Ala Arg Leu Gln Phe Thr Tyr Asn His
            500                 505                 510

Ile Gln Arg His Val Asn Asp Met Leu Gly Arg Val Ala Ile Ala Trp
        515                 520                 525

Cys Glu Leu Gln Asn His Glu Leu Thr Leu Trp Asn Glu Ala Arg Lys
    530                 535                 540

Leu Asn Pro Asn Ala Ile Ala Ser Val Thr Val Gly Arg Arg Val Ser
545                 550                 555                 560

Ala Arg Met Leu Gly Asp Val Met Ala Val Ser Thr Cys Val Pro Val
                565                 570                 575

Ala Ala Asp Asn Val Ile Val Gln Asn Ser Met Arg Ile Ser Ser Arg
            580                 585                 590

Pro Gly Ala Cys Tyr Ser Arg Pro Leu Val Ser Phe Arg Tyr Glu Asp
        595                 600                 605

Gln Gly Pro Leu Val Glu Gly Gln Leu Gly Glu Asn Asn Glu Leu Arg
    610                 615                 620

Leu Thr Arg Asp Ala Ile Glu Pro Cys Thr Val Gly His Arg Arg Tyr
625                 630                 635                 640
```

-continued

```
Phe Thr Phe Gly Gly Gly Tyr Val Tyr Phe Glu Glu Tyr Ala Tyr Ser
                645                 650                 655

His Gln Leu Ser Arg Ala Asp Ile Thr Thr Val Ser Thr Phe Ile Asp
            660                 665                 670

Leu Asn Ile Thr Met Leu Glu Asp His Glu Phe Val Pro Leu Glu Val
        675                 680                 685

Tyr Thr Arg His Glu Ile Lys Asp Ser Gly Leu Leu Asp Tyr Thr Glu
    690                 695                 700

Val Gln Arg Arg Asn Gln Leu His Asp Leu Arg Phe Ala Asp Ile Asp
705                 710                 715                 720

Thr Val Ile His Ala Asp Ala Asn Ala Ala Met Phe Ala Gly Leu Gly
                725                 730                 735

Ala Phe Phe Glu Gly Met Gly Asp Leu Gly Arg Ala Val Gly Lys Val
            740                 745                 750

Val Met Gly Ile Val Gly Gly Val Val Ser Ala Val Ser Gly Val Ser
        755                 760                 765

Ser Phe Met Ser Asn Pro Phe Gly Ala Leu Ala Val Gly Leu Leu Val
    770                 775                 780

Leu Ala Gly Leu Ala Ala Ala Phe Phe Ala Phe Arg Tyr Val Met Arg
785                 790                 795                 800

Leu Gln Ser Asn Pro Met Lys Ala Leu Tyr Pro Leu Thr Thr Lys Glu
                805                 810                 815

Leu Lys Asn Pro Thr Asn Pro Asp Ala Ser Gly Glu Gly Glu Glu Gly
            820                 825                 830

Gly Asp Phe Asp Glu Ala Lys Leu Ala Glu Ala Arg Glu Met Ile Arg
        835                 840                 845

Tyr Met Ala Leu Val Ser Ala Met Glu Arg Thr Glu His Lys Ala Lys
    850                 855                 860

Lys Lys Gly Thr Ser Ala Leu Leu Ser Ala Lys Val Thr Asp Met Val
865                 870                 875                 880

Met Arg Lys Arg Arg Asn Thr Asn Tyr Thr Gln Val Pro Asn Lys Asp
                885                 890                 895

Gly Asp Ala Asp Glu Asp Asp Leu
            900


<210> SEQ ID NO 3
<211> LENGTH: 511
<212> TYPE: PRT
<213> ORGANISM: Artificial Sequence
<220> FEATURE:
<223> OTHER INFORMATION: gC

<400> SEQUENCE: 3

Met Ala Pro Gly Arg Val Gly Leu Ala Val Val Leu Trp Ser Leu Leu
1               5                   10                  15

Trp Leu Gly Ala Gly Val Ala Gly Gly Ser Glu Thr Ala Ser Thr Gly
            20                  25                  30

Pro Thr Ile Thr Ala Gly Ala Val Thr Asn Ala Ser Glu Ala Pro Thr
        35                  40                  45

Ser Gly Ser Pro Gly Ser Ala Ala Ser Pro Glu Val Thr Pro Thr Ser
    50                  55                  60

Thr Pro Asn Pro Asn Asn Val Thr Gln Asn Lys Thr Thr Pro Thr Glu
65                  70                  75                  80

Pro Ala Ser Pro Pro Thr Thr Pro Lys Pro Thr Ser Thr Pro Lys Ser
                85                  90                  95
```

-continued

```
Pro Pro Thr Ser Thr Pro Asp Pro Lys Pro Lys Asn Asn Thr Thr Pro
            100                 105                 110

Ala Lys Ser Gly Arg Pro Thr Lys Pro Pro Gly Pro Val Trp Cys Asp
        115                 120                 125

Arg Arg Asp Pro Leu Ala Arg Tyr Gly Ser Arg Val Gln Ile Arg Cys
    130                 135                 140

Arg Phe Arg Asn Ser Thr Arg Met Glu Phe Arg Leu Gln Ile Trp Arg
145                 150                 155                 160

Tyr Ser Met Gly Pro Ser Pro Pro Ile Ala Pro Ala Pro Asp Leu Glu
                165                 170                 175

Glu Val Leu Thr Asn Ile Thr Ala Pro Pro Gly Gly Leu Leu Val Tyr
            180                 185                 190

Asp Ser Ala Pro Asn Leu Thr Asp Pro His Val Leu Trp Ala Glu Gly
        195                 200                 205

Ala Gly Pro Gly Ala Asp Pro Pro Leu Tyr Ser Val Thr Gly Pro Leu
    210                 215                 220

Pro Thr Gln Arg Leu Ile Ile Gly Glu Val Thr Pro Ala Thr Gln Gly
225                 230                 235                 240

Met Tyr Tyr Leu Ala Trp Gly Arg Met Asp Ser Pro His Glu Tyr Gly
                245                 250                 255

Thr Trp Val Arg Val Arg Met Phe Arg Pro Pro Ser Leu Thr Leu Gln
            260                 265                 270

Pro His Ala Val Met Glu Gly Gln Pro Phe Lys Ala Thr Cys Thr Ala
        275                 280                 285

Ala Ala Tyr Tyr Pro Arg Asn Pro Val Glu Phe Val Trp Phe Glu Asp
    290                 295                 300

Asp Arg Gln Val Phe Asn Pro Gly Gln Ile Asp Thr Gln Thr His Glu
305                 310                 315                 320

His Pro Asp Gly Phe Thr Thr Val Ser Thr Val Thr Ser Glu Ala Val
                325                 330                 335

Gly Gly Gln Val Pro Pro Arg Thr Phe Thr Cys Gln Met Thr Trp His
            340                 345                 350

Arg Asp Ser Val Met Phe Ser Arg Arg Asn Ala Thr Gly Leu Ala Leu
        355                 360                 365

Val Leu Pro Arg Pro Thr Ile Thr Met Glu Phe Gly Val Arg His Val
    370                 375                 380

Val Cys Thr Ala Gly Cys Val Pro Glu Gly Val Thr Phe Ala Trp Phe
385                 390                 395                 400

Leu Gly Asp Asp Pro Ser Pro Ala Ala Lys Ser Ala Val Thr Ala Gln
                405                 410                 415

Glu Ser Cys Asp His Pro Gly Leu Ala Thr Val Arg Ser Thr Leu Pro
            420                 425                 430

Ile Ser Tyr Asp Tyr Ser Glu Tyr Ile Cys Arg Leu Thr Gly Tyr Pro
        435                 440                 445

Ala Gly Ile Pro Val Leu Glu His His Gly Ser His Gln Pro Pro Pro
    450                 455                 460

Arg Asp Pro Thr Glu Arg Gln Val Ile Glu Ala Ile Glu Trp Val Gly
465                 470                 475                 480

Ile Gly Ile Gly Val Leu Ala Ala Gly Val Leu Val Val Thr Ala Ile
                485                 490                 495

Val Tyr Val Val Arg Thr Ser Gln Ser Arg Gln Arg His Arg Arg
            500                 505                 510
```

<210> SEQ ID NO 4
<211> LENGTH: 120
<212> TYPE: PRT
<213> ORGANISM: Artificial Sequence
<220> FEATURE:
<223> OTHER INFORMATION: HER2 VH

<400> SEQUENCE: 4

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 5
<211> LENGTH: 107
<212> TYPE: PRT
<213> ORGANISM: Artificial Sequence
<220> FEATURE:
<223> OTHER INFORMATION: HER2 VL

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 6
<211> LENGTH: 113
<212> TYPE: PRT
<213> ORGANISM: Artificial Sequence
<220> FEATURE:
<223> OTHER INFORMATION: EpCAM VL

<400> SEQUENCE: 6

```
Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
            20                  25                  30
```

-continued

```
Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Leu Lys
            100                 105                 110

Arg


<210> SEQ ID NO 7
<211> LENGTH: 114
<212> TYPE: PRT
<213> ORGANISM: Artificial Sequence
<220> FEATURE:
<223> OTHER INFORMATION: EpCAM VH

<400> SEQUENCE: 7

Gln Leu Val Gln Ser Gly Pro Gly Leu Val Gln Pro Gly Gly Ser Val
1               5                   10                  15

Arg Ile Ser Cys Ala Ala Ser Gly Tyr Thr Phe Thr Asn Tyr Gly Met
            20                  25                  30

Asn Trp Val Lys Gln Ala Pro Gly Lys Gly Leu Glu Trp Met Gly Trp
        35                  40                  45

Ile Asn Thr Tyr Thr Gly Glu Ser Thr Tyr Ala Asp Ser Phe Lys Gly
    50                  55                  60

Arg Phe Thr Phe Ser Leu Asp Thr Ser Ala Ser Ala Ala Tyr Leu Gln
65                  70                  75                  80

Ile Asn Ser Leu Arg Ala Glu Asp Thr Ala Val Tyr Tyr Cys Ala Arg
                85                  90                  95

Phe Ala Ile Lys Gly Asp Tyr Trp Gly Gln Gly Thr Leu Leu Thr Val
            100                 105                 110

Ser Ser


<210> SEQ ID NO 8
<211> LENGTH: 106
<212> TYPE: PRT
<213> ORGANISM: Artificial Sequence
<220> FEATURE:
<223> OTHER INFORMATION: CEA VL

<400> SEQUENCE: 8

Asp Ile Gln Met Thr Gln Ser Pro Ala Ser Leu Ser Ala Ser Val Gly
1               5                   10                  15

Asp Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Ala Lys Ala Leu Ser Glu Gly Val Pro Ser Arg Phe Ser Gly Ser
    50                  55                  60

Gly Ser Gly Thr Gln Phe Ser Leu Arg Ile Asn Ser Leu Gln Pro Glu
65                  70                  75                  80

Asp Phe Gly Asp Tyr Tyr Cys Gln His His Tyr Asn Ser Pro Tyr Thr
                85                  90                  95
```

```
Phe Gly Gly Gly Thr Lys Leu Glu Ile Lys
            100                 105


<210> SEQ ID NO 9
<211> LENGTH: 115
<212> TYPE: PRT
<213> ORGANISM: Artificial Sequence
<220> FEATURE:
<223> OTHER INFORMATION: CEA VH

<400> SEQUENCE: 9

Gln Ile Gln Leu Val Gln Ser Gly Glu Leu Lys Lys Pro Gly Glu Thr
1               5                   10                  15

Val Lys Ile Ser Cys Lys Ala Ser Gly Tyr Ser Phe Thr Asn Asp Gly
            20                  25                  30

Ile Asn Trp Val Lys Gln Ala Pro Gly Lys Gly Phe Lys Tyr Met Gly
        35                  40                  45

Trp Ile Asn Thr Ile Thr Gly Glu Pro Thr Tyr Thr Glu Asp Phe Lys
    50                  55                  60

Gly Arg Phe Ala Phe Ser Leu Glu Thr Ser Ala Ser Thr Ala Tyr Leu
65                  70                  75                  80

Gln Ile Asn Asn Leu Lys Asp Glu Asp Thr Ala Thr Phe Phe Cys Ala
                85                  90                  95

Lys Gly Thr Gly Thr Ser Ala Tyr Trp Gly Gln Gly Thr Leu Val Thr
            100                 105                 110

Val Ser Ala
        115


<210> SEQ ID NO 10
<211> LENGTH: 369
<212> TYPE: PRT
<213> ORGANISM: Artificial Sequence
<220> FEATURE:
<223> OTHER INFORMATION: gD

<400> SEQUENCE: 10

Lys Tyr Ala Leu Ala Asp Ala Ser Leu Lys Met Ala Asp Pro Asn Arg
1               5                   10                  15

Phe Arg Gly Lys Asp Leu Pro Val Leu Asp Gln Leu Thr Asp Pro Pro
            20                  25                  30

Gly Val Arg Arg Val Tyr His Ile Gln Ala Gly Leu Pro Asp Pro Phe
        35                  40                  45

Gln Pro Pro Ser Leu Pro Ile Thr Val Tyr Tyr Ala Val Leu Glu Arg
    50                  55                  60

Ala Cys Arg Ser Val Leu Leu Asn Ala Pro Ser Glu Ala Pro Gln Ile
65                  70                  75                  80

Val Arg Gly Ala Ser Glu Asp Val Arg Lys Gln Pro Tyr Asn Leu Thr
                85                  90                  95

Ile Ala Trp Phe Arg Met Gly Gly Asn Cys Ala Ile Pro Ile Thr Val
            100                 105                 110

Met Glu Tyr Thr Glu Cys Ser Tyr Asn Lys Ser Leu Gly Ala Cys Pro
        115                 120                 125

Ile Arg Thr Gln Pro Arg Trp Asn Tyr Tyr Asp Ser Phe Ser Ala Val
    130                 135                 140

Ser Glu Asp Asn Leu Gly Phe Leu Met His Ala Pro Ala Phe Glu Thr
145                 150                 155                 160

Ala Gly Thr Tyr Leu Arg Leu Val Lys Ile Asn Asp Trp Thr Glu Ile
                165                 170                 175
```

```
Thr Gln Phe Ile Leu Glu His Arg Ala Lys Gly Ser Cys Lys Tyr Ala
            180                 185                 190

Leu Pro Leu Arg Ile Pro Pro Ser Ala Cys Leu Ser Pro Gln Ala Tyr
        195                 200                 205

Gln Gln Gly Val Thr Val Asp Ser Ile Gly Met Leu Pro Arg Phe Ile
    210                 215                 220

Pro Glu Asn Gln Arg Thr Val Ala Val Tyr Ser Leu Lys Ile Ala Gly
225                 230                 235                 240

Trp His Gly Pro Lys Ala Pro Tyr Thr Ser Thr Leu Leu Pro Pro Glu
                245                 250                 255

Leu Ser Glu Thr Pro Asn Ala Thr Gln Pro Glu Leu Ala Pro Glu Asp
            260                 265                 270

Pro Glu Asp Ser Ala Leu Leu Glu Asp Pro Val Gly Thr Val Ala Pro
        275                 280                 285

Gln Ile Pro Pro Asn Trp His Ile Pro Ser Ile Gln Asp Ala Ala Thr
    290                 295                 300

Pro Tyr His Pro Pro Ala Thr Pro Asn Asn Met Gly Leu Ile Ala Gly
305                 310                 315                 320

Ala Val Gly Gly Ser Leu Leu Ala Ala Leu Val Ile Cys Gly Ile Val
                325                 330                 335

Tyr Trp Met His Arg Arg Thr Arg Lys Ala Pro Lys Arg Ile Arg Leu
            340                 345                 350

Pro His Ile Arg Glu Asp Asp Gln Pro Ser Ser His Gln Pro Leu Phe
        355                 360                 365

Tyr
```

<210> SEQ ID NO 11
<211> LENGTH: 60
<212> TYPE: DNA
<213> ORGANISM: Artificial Sequence
<220> FEATURE:
<223> OTHER INFORMATION: gD-rpsL For

<400> SEQUENCE: 11
cccaggccta ccagcagggg gtgacggtgg acagcatcgg gatgctgccc ggcctggtga 60

<210> SEQ ID NO 12
<211> LENGTH: 88
<212> TYPE: DNA
<213> ORGANISM: Artificial Sequence
<220> FEATURE:
<223> OTHER INFORMATION: gD-rpsL Rev

<400> SEQUENCE: 12
ccggcgatct tcaagctgta tacggcgacg gtgcgctggt tctcggggat tcagaagaac 60
tcgtcaagaa ggcgtgatgg cgggatcg 88

<210> SEQ ID NO 13
<211> LENGTH: 106
<212> TYPE: DNA
<213> ORGANISM: Artificial Sequence
<220> FEATURE:
<223> OTHER INFORMATION: gD R222N_F223I_mutant

<400> SEQUENCE: 13
cccaggccta ccagcagggg gtgacggtgg acagcatcgg gatgctgccc aatatcatcc 60
ccgagaacca gcgcaccgtc gccgtataca gcttgaagat cgccgg 106

-continued

<210> SEQ ID NO 14
<211> LENGTH: 74
<212> TYPE: DNA
<213> ORGANISM: Artificial Sequence
<220> FEATURE:
<223> OTHER INFORMATION: UL26/27-rpsL_For

<400> SEQUENCE: 14
gcgtgggggg gaggaaatcg gcactgacca agggggtccg ttttgtcacg tcagaagaac 60
tcgtcaagaa ggcg 74

<210> SEQ ID NO 15
<211> LENGTH: 74
<212> TYPE: DNA
<213> ORGANISM: Artificial Sequence
<220> FEATURE:
<223> OTHER INFORMATION: UL26/27-rpsL_Rev

<400> SEQUENCE: 15
aacacataaa ctcccccggg tgtccgcggc ctgtttcctc tttcctttcc ggcctggtga 60
tgatggcggg atcg 74

<210> SEQ ID NO 16
<211> LENGTH: 74
<212> TYPE: DNA
<213> ORGANISM: Artificial Sequence
<220> FEATURE:
<223> OTHER INFORMATION: UL26-tkpA_For

<400> SEQUENCE: 16
gcgtgggggg gaggaaatcg gcactgacca agggggtccg ttttgtcacg gcctcagaag 60
ccatagagcc cacc 74

<210> SEQ ID NO 17
<211> LENGTH: 74
<212> TYPE: DNA
<213> ORGANISM: Artificial Sequence
<220> FEATURE:
<223> OTHER INFORMATION: UL27-pCMV_Rev

<400> SEQUENCE: 17
aacacataaa ctcccccggg tgtccgcggc ctgtttcctc tttcctttcc tatacgcgtt 60
gacattgatt attg 74

<210> SEQ ID NO 18
<211> LENGTH: 15
<212> TYPE: PRT
<213> ORGANISM: Artificial Sequence
<220> FEATURE:
<223> OTHER INFORMATION: HER2 Linker

<400> SEQUENCE: 18

Gly Gly Gly Gly Ser Gly Gly Gly Gly Ser Gly Gly Gly Gly Ser
1 5 10 15

<210> SEQ ID NO 19
<211> LENGTH: 13
<212> TYPE: PRT
<213> ORGANISM: Artificial Sequence
<220> FEATURE:
<223> OTHER INFORMATION: HER2scFv C-terminus Linker

<400> SEQUENCE: 19

Ala Ala Ala Ser Ser Gly Gly Gly Ser Gly Ser Gly Gly
1 5 10

<210> SEQ ID NO 20
<211> LENGTH: 12
<212> TYPE: PRT
<213> ORGANISM: Artificial Sequence
<220> FEATURE:
<223> OTHER INFORMATION: HER2scFv N-terminus Linker

<400> SEQUENCE: 20

Ser Gly Gly Gly Ser Gly Ser Gly Gly Ala Ala Ala
1 5 10

<210> SEQ ID NO 21
<211> LENGTH: 27
<212> TYPE: PRT
<213> ORGANISM: Artificial Sequence
<220> FEATURE:
<223> OTHER INFORMATION: EpCAM Linker

<400> SEQUENCE: 21

Ala Thr Pro Ser His Asn Ser His Gln Val Pro Ser Ala Gly Gly Pro
1 5 10 15

Thr Ala Asn Ser Gly Thr Ser Gly Ser Glu Val
20 25

<210> SEQ ID NO 22
<211> LENGTH: 12
<212> TYPE: PRT
<213> ORGANISM: Artificial Sequence
<220> FEATURE:
<223> OTHER INFORMATION: EpCAMscFv N-terminus

<400> SEQUENCE: 22

Ala Ala Ala Ser Ser Gly Gly Gly Ser Gly Ser Gly
1 5 10

<210> SEQ ID NO 23
<211> LENGTH: 14
<212> TYPE: PRT
<213> ORGANISM: Artificial Sequence
<220> FEATURE:
<223> OTHER INFORMATION: EpCAMscFv C-terminus

<400> SEQUENCE: 23

Ser Ser Gly Gly Gly Ser Gly Ser Gly Gly Ser Ala Ala Ala
1 5 10

<210> SEQ ID NO 24
<211> LENGTH: 17
<212> TYPE: PRT
<213> ORGANISM: Artificial Sequence
<220> FEATURE:
<223> OTHER INFORMATION: CEA Linker

<400> SEQUENCE: 24

Ser Ser Gly Gly Gly Gly Ser Gly Gly Gly Gly Ser Gly Gly Gly Gly
1 5 10 15

Ser

<210> SEQ ID NO 25
<211> LENGTH: 13
<212> TYPE: PRT
<213> ORGANISM: Artificial Sequence
<220> FEATURE:

-continued

<223> OTHER INFORMATION: CEAscFv N-terminus Linker

<400> SEQUENCE: 25

Ala Ala Ala Ser Ser Gly Gly Gly Ser Gly Ser Gly Gly
1 5 10

<210> SEQ ID NO 26
<211> LENGTH: 12
<212> TYPE: PRT
<213> ORGANISM: Artificial Sequence
<220> FEATURE:
<223> OTHER INFORMATION: CEAscFv C-terminus Linker

<400> SEQUENCE: 26

Ser Ser Gly Gly Gly Ser Gly Ser Gly Ala Ala Ala
1 5 10

<210> SEQ ID NO 27
<211> LENGTH: 268
<212> TYPE: PRT
<213> ORGANISM: Artificial Sequence
<220> FEATURE:
<223> OTHER INFORMATION: HER2scFv ligand whole sequence

<400> SEQUENCE: 27

Ala Ala Ala Ser Ser Gly Gly Gly Ser Gly Ser Gly Gly Glu Val Gln
1 5 10 15

Leu Val Glu Ser Gly Gly Gly Leu Val Gln Pro Gly Gly Ser Leu Arg
20 25 30

Leu Ser Cys Ala Ala Ser Gly Phe Asn Ile Lys Asp Thr Tyr Ile His
35 40 45

Trp Val Arg Gln Ala Pro Gly Lys Gly Leu Glu Trp Val Ala Arg Ile
50 55 60

Tyr Pro Thr Asn Gly Tyr Thr Arg Tyr Ala Asp Ser Val Lys Gly Arg
65 70 75 80

Phe Thr Ile Ser Ala Asp Thr Ser Lys Asn Thr Ala Tyr Leu Gln Met
85 90 95

Asn Ser Leu Arg Ala Glu Asp Thr Ala Val Tyr Tyr Cys Ser Arg Trp
100 105 110

Gly Gly Asp Gly Phe Tyr Ala Met Asp Tyr Trp Gly Gln Gly Thr Leu
115 120 125

Val Thr Val Ser Ser Gly Gly Gly Gly Ser Gly Gly Gly Gly Ser Gly
130 135 140

Gly Gly Gly Ser Asp Ile Gln Met Thr Gln Ser Pro Ser Ser Leu Ser
145 150 155 160

Ala Ser Val Gly Asp Arg Val Thr Ile Thr Cys Arg Ala Ser Gln Asp
165 170 175

Val Asn Thr Ala Val Ala Trp Tyr Gln Gln Lys Pro Gly Lys Ala Pro
180 185 190

Lys Leu Leu Ile Tyr Ser Ala Ser Phe Leu Tyr Ser Gly Val Pro Ser
195 200 205

Arg Phe Ser Gly Ser Arg Ser Gly Thr Asp Phe Thr Leu Thr Ile Ser
210 215 220

Ser Leu Gln Pro Glu Asp Phe Ala Thr Tyr Tyr Cys Gln Gln His Tyr
225 230 235 240

Thr Thr Pro Pro Thr Phe Gly Gln Gly Thr Lys Val Glu Ile Lys Ser
245 250 255

Gly Gly Gly Ser Gly Ser Gly Gly Ser Ala Ala Ala 260 265

<210> SEQ ID NO 28
<211> LENGTH: 801
<212> TYPE: DNA
<213> ORGANISM: Artificial Sequence
<220> FEATURE:
<223> OTHER INFORMATION: HER2scFv ligand whole sequence

<400> SEQUENCE: 28
gcggccgcca gtagtggcgg tggctctggt tccggtggag aggtgcagct ggttgaatct 60
ggcggaggac tggttcagcc tggcggatct ctgagactgt cttgtgccgc cagcggcttc 120
aacatcaagg acacctacat ccactgggtc cgacaggccc ctggcaaagg acttgaatgg 180
gtcgccagaa tctaccccac caacggctac accagatacg ccgactctgt gaagggcaga 240
ttcaccatca gcgccgacac cagcaagaac accgcctacc tgcagatgaa cagcctgaga 300
gccgaggaca ccgccgtgta ctactgttct agatggggag gcgacggctt ctacgccatg 360
gattattggg gccagggcac cctggtcaca gtttctagcg gaggcggagg ttctggcggc 420
ggaggaagtg gtggcggagg ctctgatatc cagatgacac agagccccag cagcctgtct 480
gcctctgtgg gagacagagt gaccatcacc tgtagagcca gccaggacgt gaacacagcc 540
gtggcttggt atcagcagaa gcctggcaag gcccctaagc tgctgatcta cagcgccagc 600
tttctgtaca gcggcgtgcc cagcagattc agcggctcta gaagcggcac cgacttcacc 660
ctgaccataa gcagtctgca gcccgaggac ttcgccacct actactgtca gcagcactac 720
accacacctc caaccttcgg acagggcacc aaggtggaaa tcaagggtgg aggctctggt 780
tccggtggat ccgcggccgc g 801

<210> SEQ ID NO 29
<211> LENGTH: 280
<212> TYPE: PRT
<213> ORGANISM: Artificial Sequence
<220> FEATURE:
<223> OTHER INFORMATION: EpCAMscFv ligand whole sequence

<400> SEQUENCE: 29

Ala Ala Ala Ser Ser Gly Gly Gly Ser Gly Ser Gly Asp Ile Gln Met
1 5 10 15

Thr Gln Ser Pro Ser Ser Leu Ser Ala Ser Val Gly Asp Arg Val Thr
20 25 30

Ile Thr Cys Arg Ser Thr Lys Ser Leu Leu His Ser Asn Gly Ile Thr
35 40 45

Tyr Leu Tyr Trp Tyr Gln Gln Lys Pro Gly Lys Ala Pro Lys Leu Leu
50 55 60

Ile Tyr Gln Met Ser Asn Leu Ala Ser Gly Val Pro Ser Arg Phe Ser
65 70 75 80

Ser Ser Gly Ser Gly Thr Asp Phe Thr Leu Thr Ile Ser Ser Leu Gln
85 90 95

Pro Glu Asp Phe Ala Thr Tyr Tyr Cys Ala Gln Asn Leu Glu Ile Pro
100 105 110

Arg Thr Phe Gly Gln Gly Thr Lys Val Glu Leu Lys Arg Ala Thr Pro
115 120 125

Ser His Asn Ser His Gln Val Pro Ser Ala Gly Gly Pro Thr Ala Asn
130 135 140

Ser Gly Thr Ser Gly Ser Glu Val Gln Leu Val Gln Ser Gly Pro Gly
145 150 155 160

```
Leu Val Gln Pro Gly Gly Ser Val Arg Ile Ser Cys Ala Ala Ser Gly
                165                 170                 175

Tyr Thr Phe Thr Asn Tyr Gly Met Asn Trp Val Lys Gln Ala Pro Gly
            180                 185                 190

Lys Gly Leu Glu Trp Met Gly Trp Ile Asn Thr Tyr Thr Gly Glu Ser
        195                 200                 205

Thr Tyr Ala Asp Ser Phe Lys Gly Arg Phe Thr Phe Ser Leu Asp Thr
    210                 215                 220

Ser Ala Ser Ala Ala Tyr Leu Gln Ile Asn Ser Leu Arg Ala Glu Asp
225                 230                 235                 240

Thr Ala Val Tyr Tyr Cys Ala Arg Phe Ala Ile Lys Gly Asp Tyr Trp
                245                 250                 255

Gly Gln Gly Thr Leu Leu Thr Val Ser Ser Ser Ser Gly Gly Gly Ser
            260                 265                 270

Gly Ser Gly Gly Ser Ala Ala Ala
        275                 280


<210> SEQ ID NO 30
<211> LENGTH: 840
<212> TYPE: DNA
<213> ORGANISM: Artificial Sequence
<220> FEATURE:
<223> OTHER INFORMATION: EpCAMscFv ligand whole sequence

<400> SEQUENCE: 30

gcggccgcca gtagtggcgg tggctctggt tccggtgata tccagatgac ccagtccccg     60

tcctccctga gtgcttctgt tggtgaccgt gttaccatca cctgccgttc caccaaatcc    120

ctcctgcact ccaacggtat cacctacctt tattggtatc aacagaaacc gggtaaagct    180

ccgaaacttc tgatctacca gatgtccaac ctggcttccg gtgttccgtc tcgtttctcc    240

agttctggtt ctggtaccga cttcaccctg accatctctt ctctgcagcc ggaagacttc    300

gctacctact actgcgctca gaacctggaa atcccgcgta ccttcggtca gggtaccaaa    360

gttgaactta agcgcgctac cccgtctcac aactcccacc aggttccatc cgcaggcggt    420

ccgactgcta actctggaac tagtggatcc gaagtacagc tggttcagtc cggcccgggt    480

cttgttcaac cgggtggttc cgttcgtatc tcttgcgctg cttctggtta cacgttcacc    540

aactacggca tgaactgggt caaacaggct ccgggtaaag gcctggaatg gatgggctgg    600

atcaacacct acaccggtga atccacctac gctgactcct tcaaaggtcg cttcactttc    660

tccctcgaca caagtgctag tgctgcatac ctccaaatca actcgctgcg tgcagaggat    720

acagcagtct attactgcgc ccgtttcgct atcaaaggtg actactgggg tcaaggcacg    780

ctgctgaccg tttcctcgtc ttccggtgga ggctctggtt ccggtggatc cgcggccgcg    840


<210> SEQ ID NO 31
<211> LENGTH: 262
<212> TYPE: PRT
<213> ORGANISM: Artificial Sequence
<220> FEATURE:
<223> OTHER INFORMATION: CEAscFv ligand whole sequence

<400> SEQUENCE: 31

Ala Ala Ala Ser Ser Gly Gly Gly Ser Gly Ser Gly Gly Asp Ile Gln
1               5                   10                  15

Met Thr Gln Ser Pro Ala Ser Leu Ser Ala Ser Val Gly Asp Thr Val
            20                  25                  30
```

-continued

```
Thr Ile Thr Cys Arg Ala Ser Glu Asn Ile Tyr Ser Tyr Leu Ala Trp
        35                  40                  45

Tyr Gln Gln Lys Gln Gly Lys Ser Pro Gln Leu Leu Val Tyr Ala Lys
    50                  55                  60

Ala Leu Ser Glu Gly Val Pro Ser Arg Phe Ser Gly Ser Gly Ser Gly
65                  70                  75                  80

Thr Gln Phe Ser Leu Arg Ile Asn Ser Leu Gln Pro Glu Asp Phe Gly
                85                  90                  95

Asp Tyr Tyr Cys Gln His His Tyr Asn Ser Pro Tyr Thr Phe Gly Gly
            100                 105                 110

Gly Thr Lys Leu Glu Ile Lys Ser Ser Gly Gly Gly Gly Ser Gly Gly
        115                 120                 125

Gly Gly Ser Gly Gly Gly Gly Ser Gln Ile Gln Leu Val Gln Ser Gly
    130                 135                 140

Glu Leu Lys Lys Pro Gly Glu Thr Val Lys Ile Ser Cys Lys Ala Ser
145                 150                 155                 160

Gly Tyr Ser Phe Thr Asn Asp Gly Ile Asn Trp Val Lys Gln Ala Pro
                165                 170                 175

Gly Lys Gly Phe Lys Tyr Met Gly Trp Ile Asn Thr Ile Thr Gly Glu
            180                 185                 190

Pro Thr Tyr Thr Glu Asp Phe Lys Gly Arg Phe Ala Phe Ser Leu Glu
        195                 200                 205

Thr Ser Ala Ser Thr Ala Tyr Leu Gln Ile Asn Asn Leu Lys Asp Glu
    210                 215                 220

Asp Thr Ala Thr Phe Phe Cys Ala Lys Gly Thr Gly Thr Ser Ala Tyr
225                 230                 235                 240

Trp Gly Gln Thr Leu Val Thr Val Ser Ala Ser Ser Gly Gly Gly Ser
                245                 250                 255

Gly Ser Gly Ala Ala Ala
            260
```

<210> SEQ ID NO 32
<211> LENGTH: 801
<212> TYPE: DNA
<213> ORGANISM: Artificial Sequence
<220> FEATURE:
<223> OTHER INFORMATION: CEAscFv ligand whole sequence

<400> SEQUENCE: 32

```
gcggccgcca gtagtggcgg tggctctggt tccggtggag aggtgcagct ggttgaatct     60

ggcggaggac tggttcagcc tggcggatct ctgagactgt cttgtgccgc cagcggcttc    120

aacatcaagg acacctacat ccactgggtc cgacaggccc ctggcaaagg acttgaatgg    180

gtcgccagaa tctaccccac caacggctac accagatacg ccgactctgt gaagggcaga    240

ttcaccatca gcgccgacac cagcaagaac accgcctacc tgcagatgaa cagcctgaga    300

gccgaggaca ccgccgtgta ctactgttct agatggggag gcgacggctt ctacgccatg    360

gattattggg gccagggcac cctggtcaca gtttctagcg gaggcggagg ttctggcggc    420

ggaggaagtg gtggcggagg ctctgatatc cagatgacac agagccccag cagcctgtct    480

gcctctgtgg gagacagagt gaccatcacc tgtagagcca gccaggacgt gaacacagcc    540

gtggcttggt atcagcagaa gcctggcaag gcccctaagc tgctgatcta cagcgccagc    600

tttctgtaca gcggcgtgcc cagcagattc agcggctcta gaagcggcac cgacttcacc    660

ctgaccataa gcagtctgca gcccgaggac ttcgccacct actactgtca gcagcactac    720
```

-continued

```
accacacctc caaccttcgg acagggcacc aaggtggaaa tcaagtcttc cggtggaggc     780

tctggttccg gtgcggccgc g                                               801


<210> SEQ ID NO 33
<211> LENGTH: 73
<212> TYPE: DNA
<213> ORGANISM: Artificial Sequence
<220> FEATURE:
<223> OTHER INFORMATION: gH29/30-rpsL-neo_For

<400> SEQUENCE: 33

tcgtgggggt tattcttttg ggcgttgcgt ggggtcaggt ccacgactgg ggcctggtga      60

tgatggcggg atc                                                         73


<210> SEQ ID NO 34
<211> LENGTH: 74
<212> TYPE: DNA
<213> ORGANISM: Artificial Sequence
<220> FEATURE:
<223> OTHER INFORMATION: gH29/30-rpsL-neo_Rev

<400> SEQUENCE: 34

ttcgtgtcgc gccagtacat gcggtccatg cccaggccat ccaaaaacca tcagaagaac      60

tcgtcaagaa ggcg                                                        74


<210> SEQ ID NO 35
<211> LENGTH: 22
<212> TYPE: DNA
<213> ORGANISM: Artificial Sequence
<220> FEATURE:
<223> OTHER INFORMATION: gH29/30-scFv_For

<400> SEQUENCE: 35

tcgtgggggt tattcttttg gg                                               22


<210> SEQ ID NO 36
<211> LENGTH: 21
<212> TYPE: DNA
<213> ORGANISM: Artificial Sequence
<220> FEATURE:
<223> OTHER INFORMATION: gH29/30_scFv_Rev

<400> SEQUENCE: 36

ttcgtgtcgc gccagtacat g                                                21
```